United States Patent [19]
Lee

[11] Patent Number: 6,033,427
[45] Date of Patent: Mar. 7, 2000

[54] METHOD AND DEVICE FOR PERCUTANEOUS SEALING OF INTERNAL PUNCTURE SITES

[76] Inventor: Benjamin I. Lee, 4911 Van Ness St. NW., Washington, D.C. 20016

[21] Appl. No.: 09/226,717

[22] Filed: Jan. 7, 1999

Related U.S. Application Data

[60] Provisional application No. 60/070,695, Jan. 7, 1998.
[51] Int. Cl.$^7$ ..................... A61B 17/00
[52] U.S. Cl. ............. 606/213; 606/214; 604/51; 604/59; 604/15; 604/285
[58] Field of Search ................... 606/213–215; 604/15, 51, 59, 60, 100, 285

[56] References Cited

U.S. PATENT DOCUMENTS

| | | | |
|---|---|---|---|
| 4,874,368 | 10/1989 | Miller et al. | 604/82 |
| 5,219,328 | 6/1993 | Morse et al. | 604/49 |
| 5,222,974 | 6/1993 | Kensey et al. | 606/213 |
| 5,282,827 | 2/1994 | Kensey et al. | 606/215 |
| 5,292,332 | 3/1994 | Lee | 606/213 |
| 5,312,435 | 5/1994 | Nash et al. | 606/213 |
| 5,318,524 | 6/1994 | Morse et al. | 604/82 |
| 5,441,517 | 8/1995 | Kensey et al. | 606/213 |
| 5,486,195 | 1/1996 | Myers et al. | 606/213 |
| 5,549,633 | 8/1996 | Evans et al. | 606/139 |
| 5,662,681 | 9/1997 | Nash et al. | 606/213 |
| 5,676,689 | 10/1997 | Kensey et al. | 606/213 |
| 5,681,334 | 10/1997 | Evans et al. | 606/148 |
| 5,700,277 | 12/1997 | Nash et al. | 606/213 |
| 5,707,393 | 1/1998 | Kensey et al. | 606/213 |
| 5,728,114 | 3/1998 | Evans et al. | 606/148 |
| 5,741,223 | 4/1998 | Jazen et al. | 604/15 |
| 5,810,885 | 9/1998 | Zinger | 606/213 |
| 5,830,130 | 11/1998 | Janzen et al. | 606/213 |
| 5,906,631 | 5/1999 | Imran | 606/213 |
| 5,928,266 | 7/1999 | Kontos | 604/106 |
| 5,941,897 | 8/1999 | Myers | 606/213 |
| 5,948,425 | 9/1999 | Janzen et al. | 606/213 |

Primary Examiner—Gary Jackson
Attorney, Agent, or Firm—Pillsbury Madison & Sutro LLP

[57] ABSTRACT

The present invention relates to a device for percutaneously sealing of an internal puncture site comprising a tissue portion having a puncture formed therethrough. A locating device is mounted for longitudinal movement relative to a guide wire towards and away from the puncture site. Delivery structure has a distal end portion and is mounted for longitudinal movement relative to the guide wire. A tubular puncture site engaging member has a distal end portion and is mounted exteriorly of the delivery structure for longitudinal movement relative to the guide wire. A supply of fluid thrombogenic material which will be capable of promoting clotting when delivered to the puncture site is provided. The delivery structure has a fluid passageway open to the distal end portion thereof and communicated to the supply of fluid thrombogenic material. The locating device and the puncture site engaging member are positioned with respect to one another such that they can be moved together towards the puncture site. The locating device transmits a signal to the user indicating that the distal end portion of the puncture site engaging member is engaged with the tissue portion in surrounding relation with respect to the puncture. The distal end portion of the delivery structure can be positioned adjacent the puncture site and the fluid thrombogenic material can then be delivered from the supply to the puncture site through the fluid passageway. The puncture site engaging member is constructed and arranged such that the distal end portion thereof will surround the fluid thrombogenic material being delivered to the puncture site so as to prevent the material from flowing away from the puncture site when the distal end portion of the puncture site engaging member is engaged with the tissue portion in surrounding relation with respect to the puncture, thereby allowing the material to promote clotting and seal the puncture. The present invention also relates to a method for percutaneously sealing internal punctures sites and to a sealing device having improved locating device for properly positioning the device with respect to the puncture site. Further, the present invention is well-suited for application to arterial puncture sites.

76 Claims, 14 Drawing Sheets

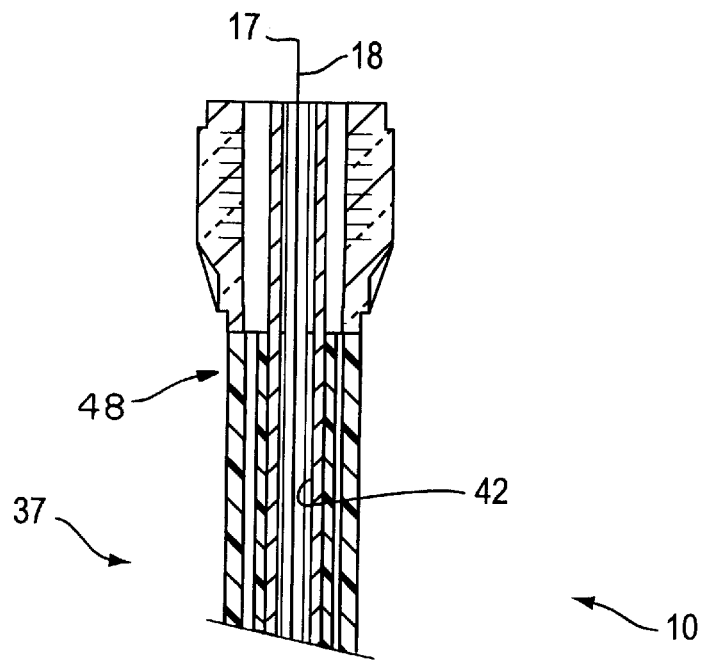
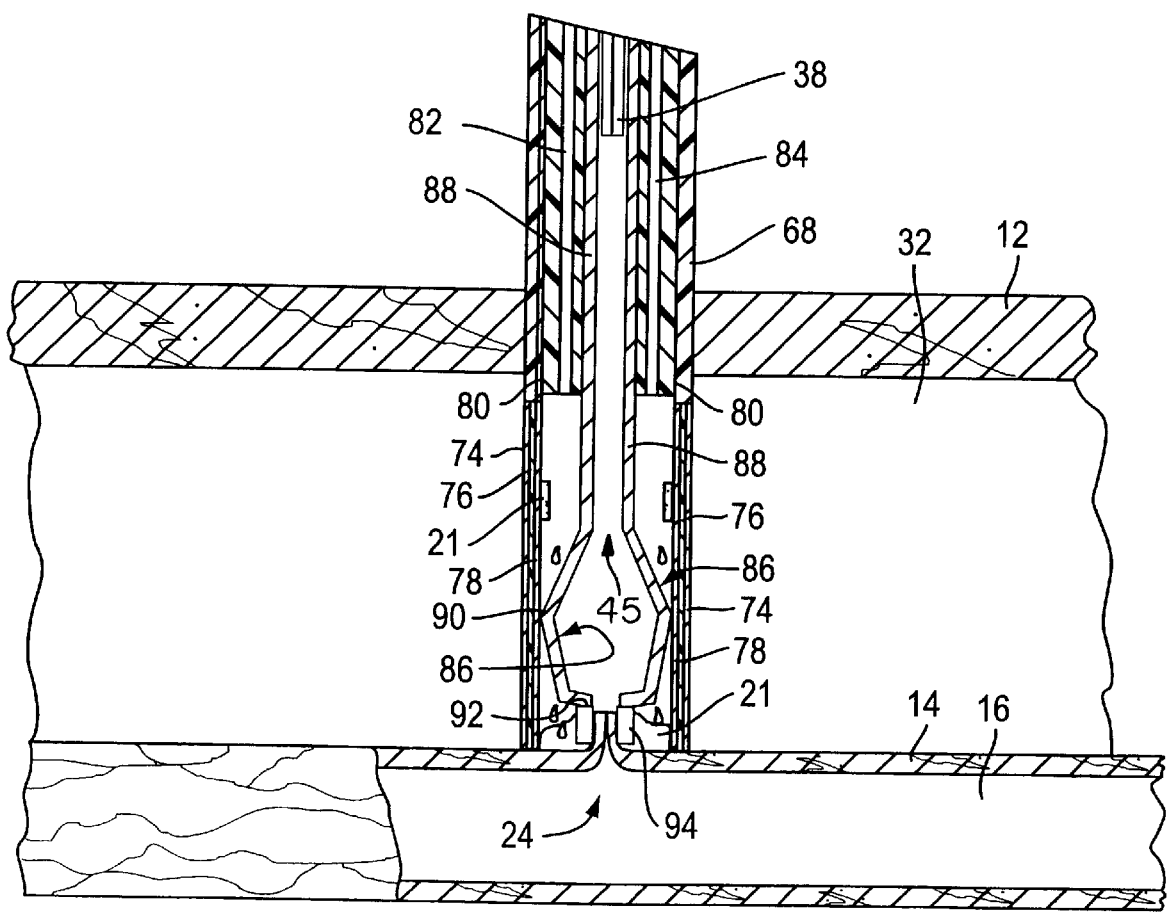
FIG.11

METHOD AND DEVICE FOR PERCUTANEOUS SEALING OF INTERNAL PUNCTURE SITES

The present application claims priority from U.S. Provisional patent application Ser. No. 60/070,695, filed Jan. 7, 1998, the entirety of which is hereby incorporated into the present application by reference.

The present invention relates to both a method and a device for percutaneously sealing an internal puncture site. The present invention is best suited for sealing puncture sites formed in blood vessels, but may be applied to other internal lumens, cavities, and organs.

In conventional angioplasty, angiography, and intravascular and intracardiac procedures, a needle, such a Seldinger or Argon needle, is inserted through the skin and into a blood vessel, such as the femoral artery. With the tip of the needle disposed in the vessel, a flexible guide wire is advanced through the needle and into the vessel. When the wire is in place, the needle is removed and an arterial dilator and an arterial sheath are advanced along the wire, through the skin, and then into the vessel. An angiographic catheter or other intravascular device may then be advanced through the sheath and along the guide wire to a desired target site. Once the procedure is completed, the device, sheath, and wire are removed and medical personnel must then apply pressure to the puncture site to assist the body's natural clotting process until hemostasis has been achieved.

Typically, such compression can take between twenty minutes to forty-five minutes before sufficient hemostasis is achieved. Afterwards, the patient is required to remain inactive for six to eight hours following the procedure, typically occupying a hospital bed during this time. Then the patient cannot resume normal activity for one or two additional days. Taking into account the fact that over 3,000,000 such procedures take place annually in the U.S. and factoring in the associated recovery period costs, including the hospital stay costs and lost time following the hospital stay before normal activities can be resumed by patients, the economic impact of such procedures are quite considerable.

Various devices and methods have been proposed for percutaneously sealing arterial puncture sites in such a way so as to avoid the need for prolonged manual compression and/or a prolonged recovery time. One such device is disclosed in U.S. Pat. No. 5,222,974, assigned to Kensey Nash Corp.

The '974 patent discloses a device which includes an introducer sheath, a length of filament, a tamping member, and a closure device. The closure device includes an anchoring member and a plug of collagen foam, the anchoring member and the plug being attached to the distal end of the filament. To affect hemostasis using this device, the introducer sheath is inserted into the blood vessel and the anchoring member is moved outwardly from the distal end of the introducer sheath. The introducer sheath is withdrawn to move the anchoring member into engagement with the interior surface of the blood vessel wall and then is further retracted to expose the collagen plug. The tamping member is then moved forwardly along the filament to deform the plug against the puncture site. During this tamping member movement, the anchoring member remains inside the blood vessel and, in effect, causes the vessel wall and the plug to be squeezed together as a result of being attached to the end of the filament. U.S. Pat. Nos. 5,707,393, 5,700,277, 5,676, 689, 5,662,681, 5,441,517, and 5,312,435, all assigned to Kensey Nash, disclose similar devices.

A significant disadvantage of the device disclosed by the '974 patent is that the anchoring member is disposed inside the blood vessel and remains there after the procedure has been completed. As a result, the anchoring member may break free from the filament and move along in the blood vessel. Further, the anchoring member may have an increased effective size as a result of blood coagulating on it, thus resulting in the anchoring member being larger than would normally be anticipated as it floats along within the blood vessel.

Thus, there exists a need for an improved and effective way of sealing percutaneous puncture sites which does not suffer the disadvantages associated with positioning part of the closure material inside the blood vessel. To meet this need, one aspect of the present invention provides a device for percutaneously sealing of an internal puncture site comprising a tissue portion having a puncture formed therethrough, the puncture site being accessible through a perforation formed through the skin and subcutaneous tissue of a living being with an elongated guide wire being inserted through the perforation and into the puncture. The device comprises a locating device constructed and arranged to be mounted for longitudinal movement relative to the guide wire towards and away from the puncture site and a supply of fluid thrombogenic material which will be capable of promoting clotting when delivered to the puncture site.

Delivery structure has a distal end portion and is constructed and arranged to be mounted for longitudinal movement relative to the guide wire towards and away from the puncture site. The delivery structure has a fluid passageway open to the distal end portion thereof and communicated to the supply of fluid thrombogenic material. Two such fluid passageways is preferred, but one may be used. A tubular puncture site engaging member has a distal end portion and is mounted exteriorly of the delivery structure for longitudinal movement relative to the guide wire towards and away from the puncture site. The locating device and the puncture site engaging member are constructed and arranged to be positioned with respect to one another such that the puncture site engaging member and the locating device can be moved together longitudinally towards the puncture site along the guide wire. The locating device is constructed and arranged to transmit a signal to the user indicating that the distal end portion of the puncture site engaging member is engaged with the tissue portion of the puncture site in surrounding relation with respect to the puncture.

The delivery structure is constructed and arranged such that the distal end portion of the delivery structure can be positioned adjacent the puncture site and the fluid thrombogenic material can be delivered from the supply to the puncture site through the fluid passageway of the delivery structure when the distal end portion of the puncture site engaging member is engaged with the aforesaid tissue portion in surrounding relation with respect to the puncture. The puncture site engaging member is constructed and arranged such that the distal end portion thereof will surround the fluid thrombogenic material being delivered to the puncture site so as to prevent the material from flowing away from the puncture site when the distal end portion of the puncture site engaging member is engaged with the tissue portion in surrounding relation with respect to the puncture, thereby allowing the material to promote clotting and seal the puncture.

A related aspect of the present invention provides a method for percutaneously sealing of an internal puncture site comprising providing a locating device, providing a supply of fluid thrombogenic material which will be capable of promoting clotting when delivered to the puncture site, and providing delivery structure having a distal end portion.

The delivery structure has a fluid passageway open to the distal end portion thereof and communicated to the supply of fluid thrombogenic material. Again, two such fluid passageways may be used, but one is preferred. A puncture site engaging member having a distal end portion is provided and is mounted exteriorly of the delivery structure and positioned with respect to the locating device such that the puncture site engaging member and the locating device can be moved longitudinally together along the guide wire toward the puncture site.

The puncture site engaging member and the locating device are then moved longitudinally along the guide wire towards the puncture site until the locating device transmits a signal to the user indicating that the distal end portion of the puncture site engaging member is engaged with a tissue portion of the puncture site in surrounding relation with respect to the puncture. The fluid thrombogenic material is thereafter delivered from the supply to the puncture site through the fluid passageway(s) and the distal end portion of the puncture site engaging member is maintained in engagement with the tissue portion as the fluid thrombogenic material is being delivered such that the distal end portion of the puncture site engaging member surrounds the fluid thrombogenic material being delivered to the puncture site so as to prevent the material from flowing away from the puncture site, thereby allowing the material to promote clotting and seal the puncture. Preferably, both the device and the method according to these aspects of the invention are used to percutaneously seal punctures in blood vessel walls; however the principles of the present invention can be applied to other tissue planes, lumens, organs, and cavities.

Yet another aspect of the present invention relates to the provision of an improved locating device. Existing devices for percutaneous sealing often incorporate a locating member or introducer sheath with a single port on the distal end thereof and a proximally extending tube connected to the port. Blood flowing through a vessel will flow into the port and proximally through the tube so that the user can verify the port is disposed inside the blood vessel. For example, U.S. Pat. No. 5,282,827, assigned to Kensey Nash, discloses an introducer sheath with such an arrangement. To properly position the introducer sheath of the '827 patent with respect to the puncture, the distal end of the sheath is inserted into the puncture until blood is seen flowing proximally in the tube, and then retracted until the blood is no longer seen in the tube. However, there is no way to tell whether the sheath has been retracted too far outside the blood vessel because this arrangement provides only one reference point for locating the sheath, and hence the remaining components of the device's closure structure. Thus, the device is not capable of indicating where it is in relation to the vessel wall—it can only indicate whether the single port is located inside or outside the vessel.

Accordingly, there exists the need for a device for percutaneously sealing an internal puncture site with an improved locating device. To meet this need, the present invention provides a sealing device for percutaneously sealing of an internal puncture site comprising closure structure constructed and arranged to seal the puncture in response to manual operation when the sealing device is in a proper operating position with respect to the puncture site. A locating device has a distal end portion with a distal port and a proximal port spaced apart generally longitudinally and open to the exterior of the distal end portion thereof. The locating device is constructed and arranged to be mounted for longitudinal movement relative to the guide wire towards and away from the puncture site and defines first and second fluid passageways connected to the locating distal port and the proximal port, respectively.

The distal port and the first fluid passageway are constructed and arranged such that, when the distal port is positioned interiorly of the puncture site, fluid flowing interiorly of the puncture site will flow into the distal port and proximally through the first fluid passageway. The proximal port and the second fluid passageway are constructed and arranged such that, when the proximal port is positioned interiorly of the puncture site, fluid flowing interiorly of the puncture site will flow into the proximal port and proximally through the second fluid passageway. The locating device is constructed and arranged to be moved longitudinally along the guide wire towards the puncture site whereby only the distal port and not the proximal port will be positioned interiorly of the puncture site when the sealing device has reached the proper operating position thereof with respect to the puncture site so that the presence of fluid flowing proximally within the first fluid passageway and the absence of fluid flowing proximally within the second fluid passageway will indicate that the sealing device is in the proper operating position with respect to the puncture site. The principles of this aspect of the invention can also be applied both to blood vessels and other tissue planes, organs, cavities, and lumens.

The device constructed in accordance with this aspect of the invention functions advantageously over existing devices because the locating device provides two reference points which cooperate to provide an indication of proper positioning. It is contemplated that the locating device of this inventive aspect can be used in conjunction with any conceivable element, component, or structure which plays a role in the sealing of the puncture. For example, the locating device could be incorporated into the device of the '827 patent or any of the other aforementioned Kensey Nash patents, the entirety of each being hereby incorporated into the present application by reference, with the anchor and filament arrangement functioning as the closure structure. Also, the closure structure could be a stapling mechanism, a suturing arrangement, or any other suitable sealing device. Thus, although the following preferred embodiments utilize a delivery structure and a puncture site engaging member to affect the sealing, among other components, the closure structure encompassed within this aspect of the invention is not limited to such an arrangement.

Other objects, features, and advantages will become apparent from the following detailed description, the accompanying drawings, and the appended claims.

IN THE DRAWINGS

Figure 6:
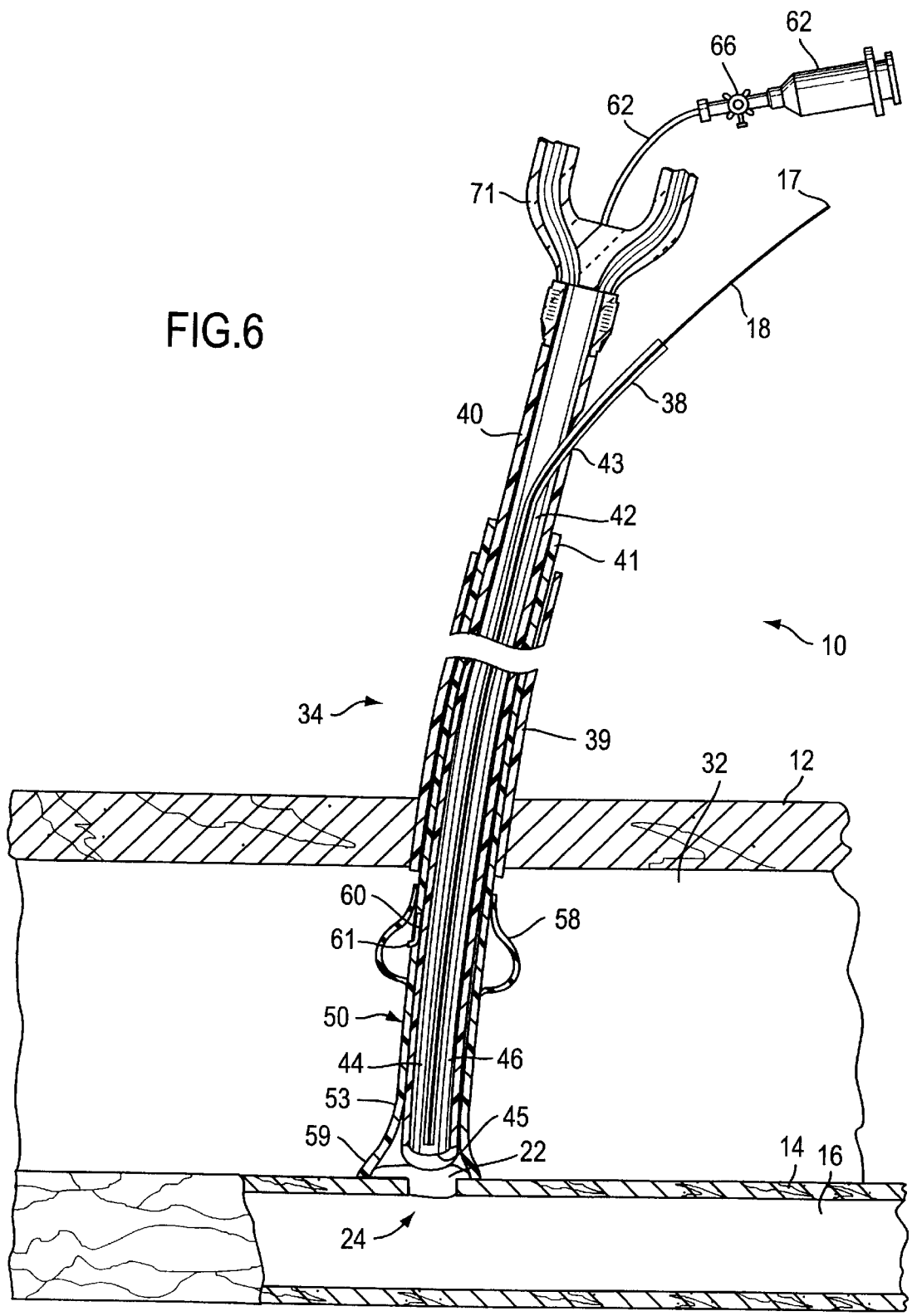
Figure 7:
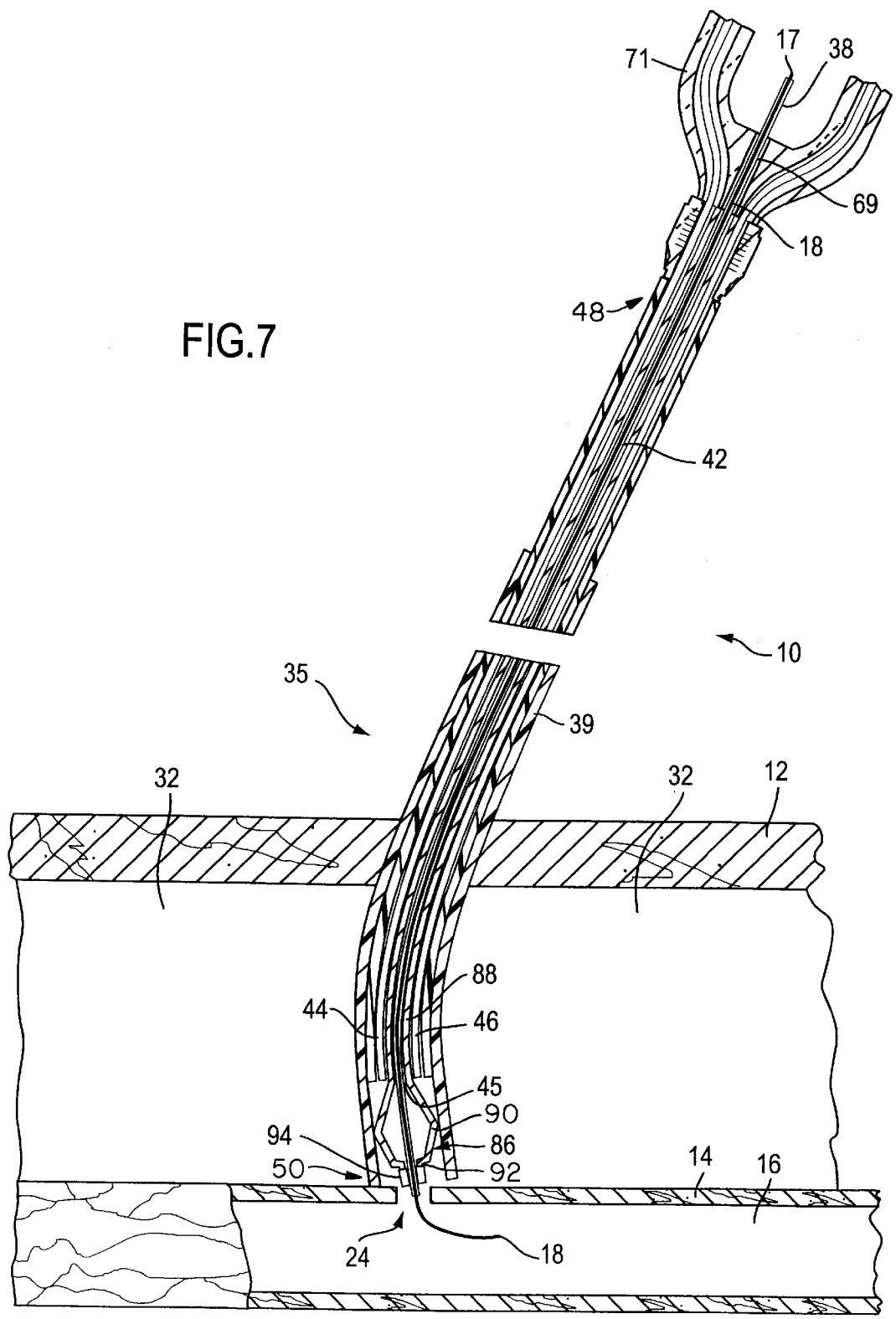
Figure 8:
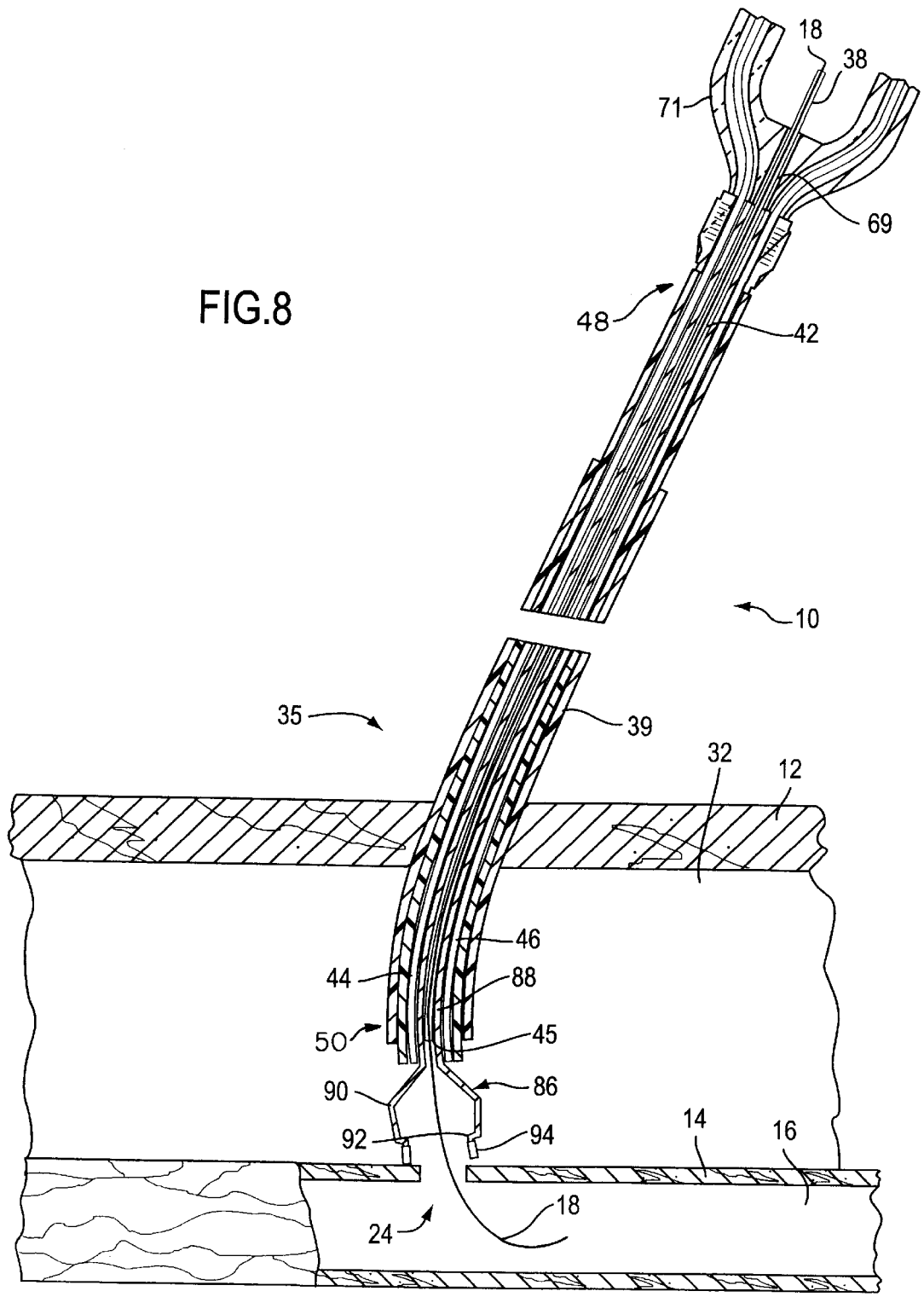
Figure 9:
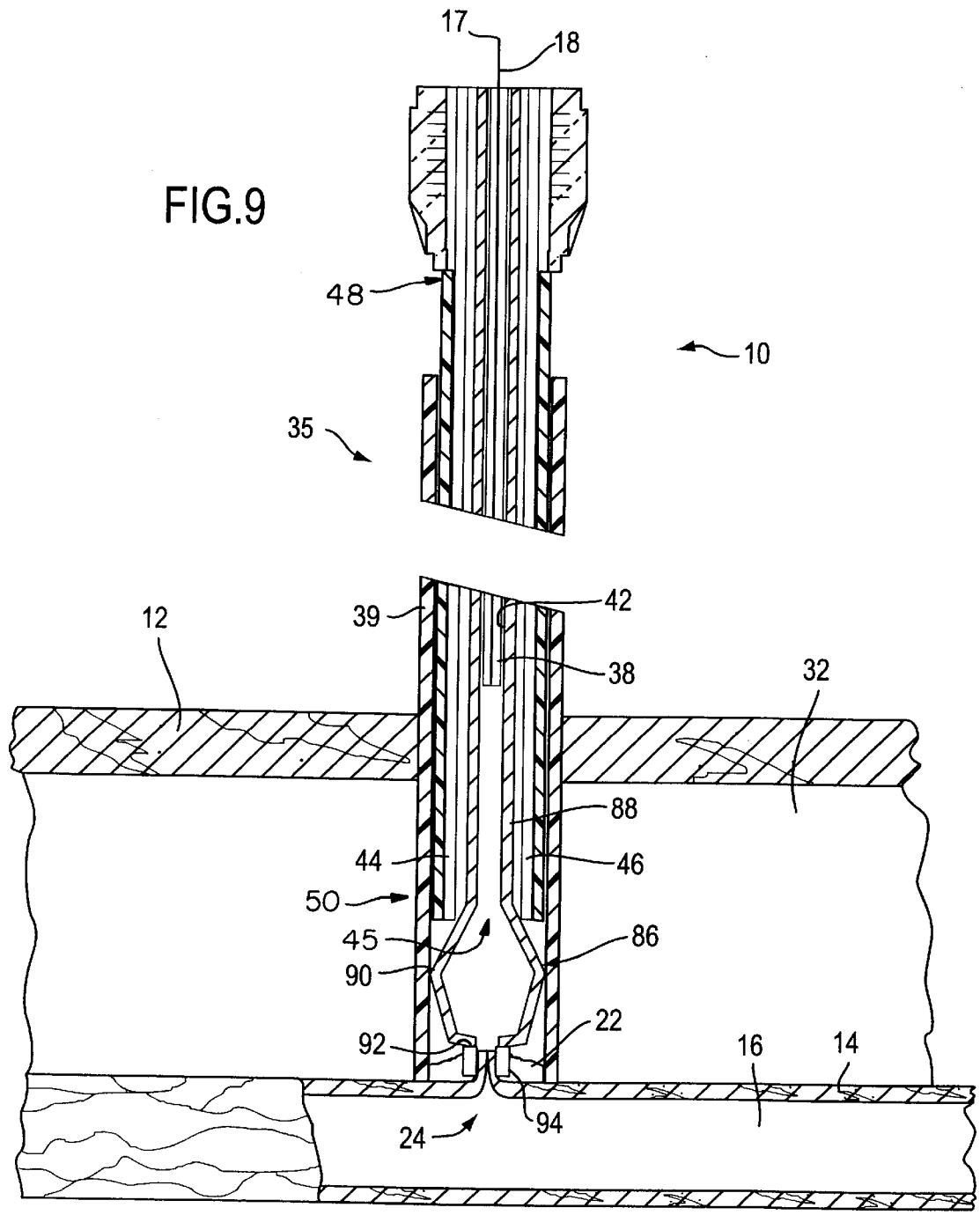
Figure 10:
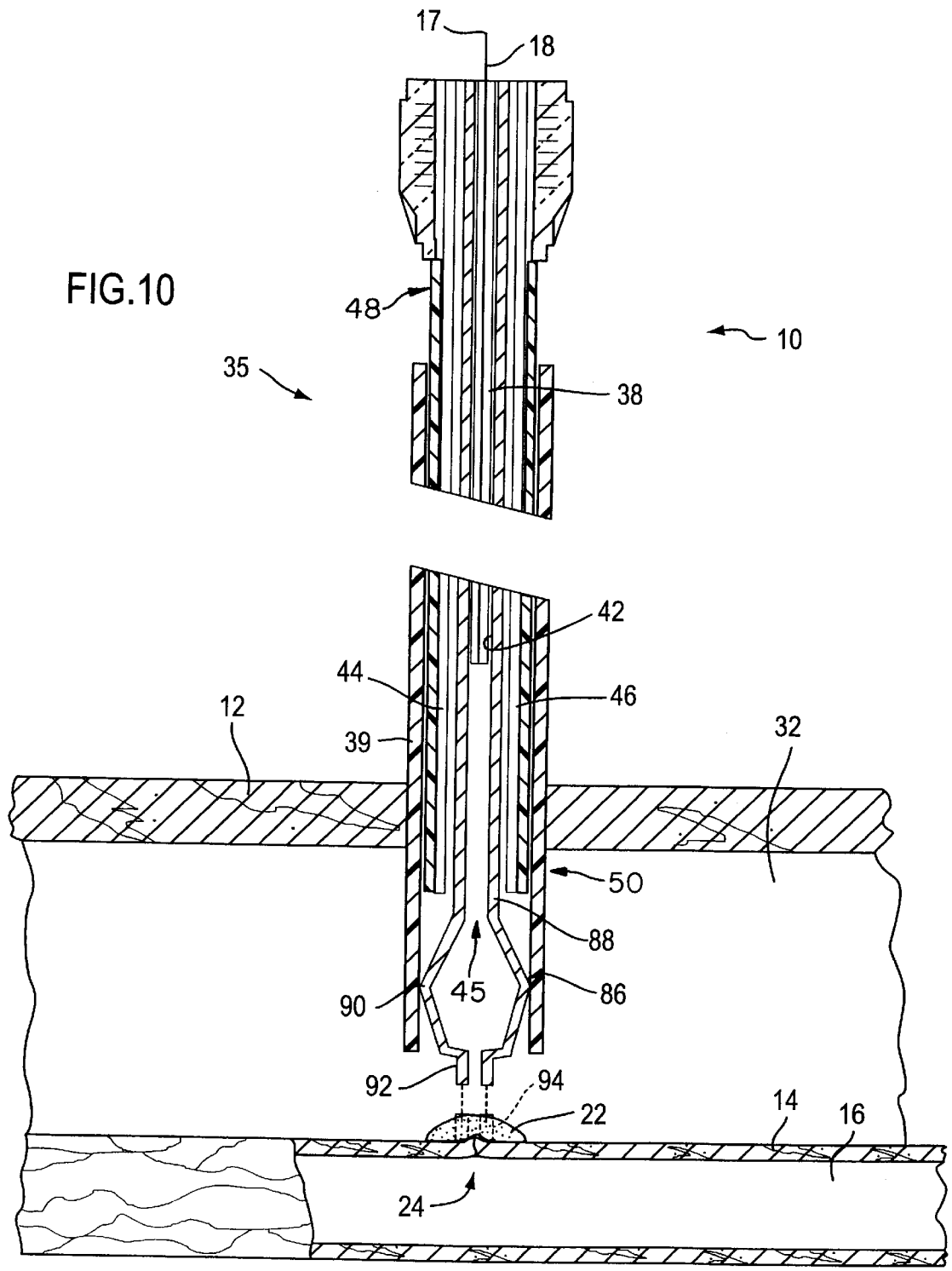
Figure 12:
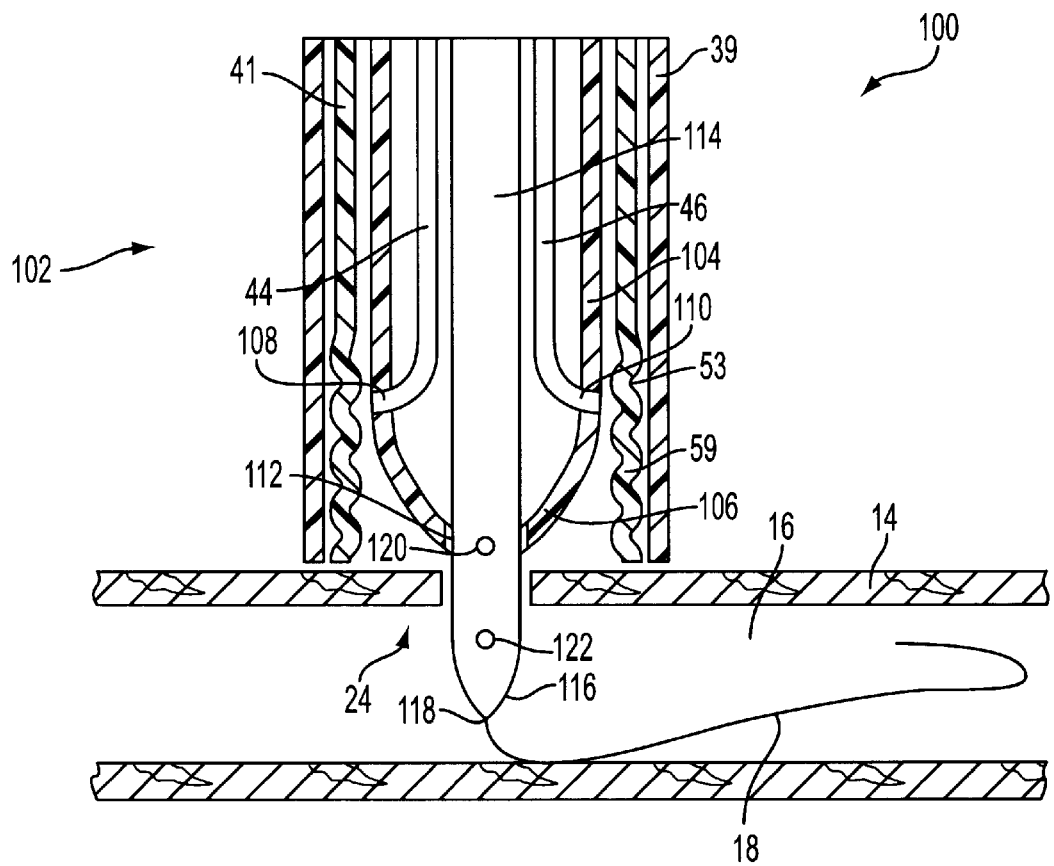
Figure 13:
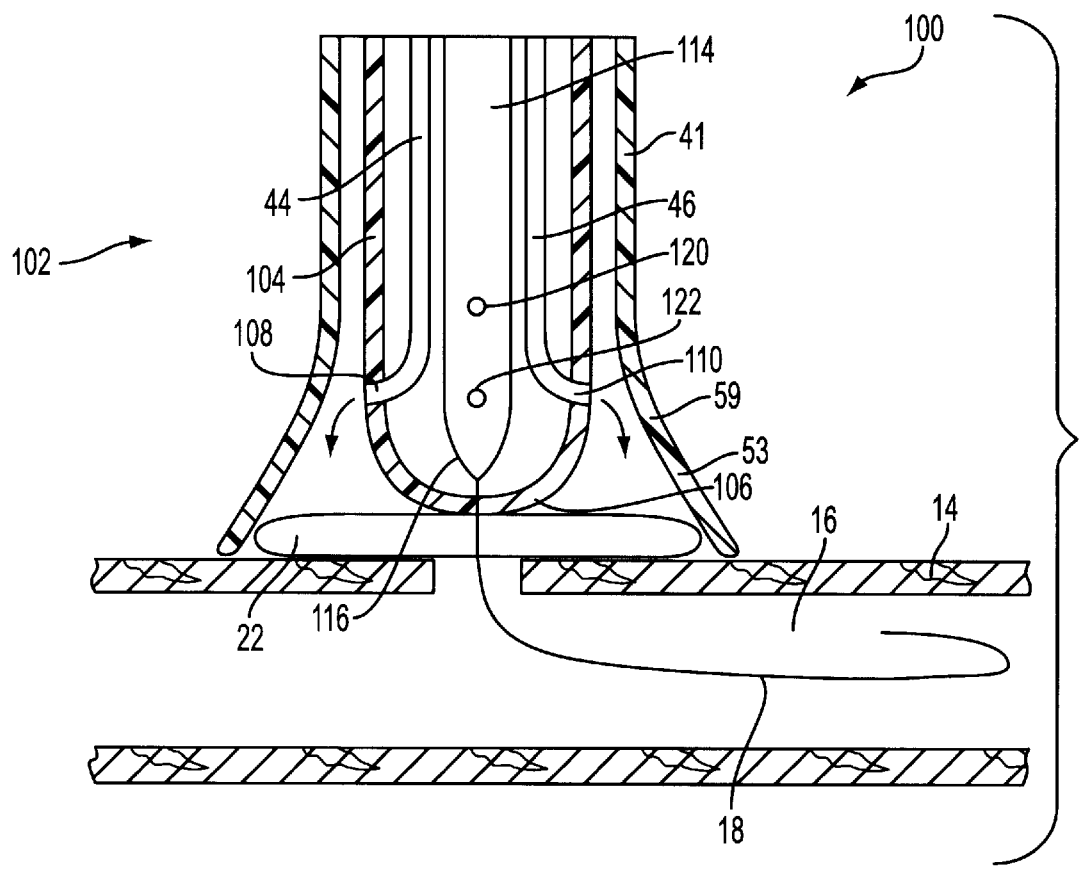
Figure 14:
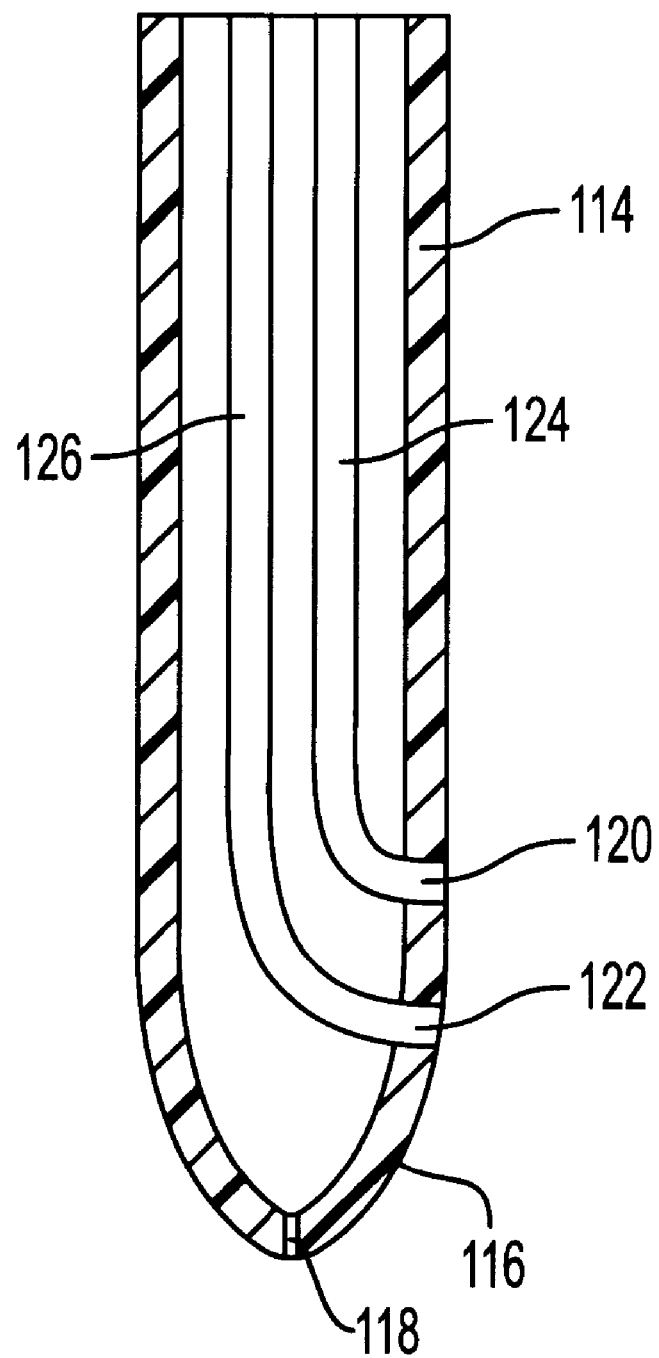

FIG. 6 is a side elevational view in partial section of a portion of the hemostatic device constructed in accordance with the first embodiment of the invention, shown with a cone shaped structure thereof in an open configuration over the puncture site in the arterial lumen which puncture site is sealed with a fibrin glue and from which puncture site a guide wire has been removed and shown with a balloon in an inflated configuration;

FIG. 7 is a side elevational view in partial section of a portion of the hemostatic device constructed in accordance with a second embodiment of the invention, shown with a thin hollow tube thereof partially within the arterial lumen and with a pair of pincher members thereof maintained in a closed position by an outer sheath member;

FIG. 8 is a side elevational view in partial section of a portion of the hemostatic device constructed in accordance with the second embodiment of the invention, shown with a thin hollow tube thereof in a retracted position relative to the arterial lumen and shown with a pair of pincher members thereof in an open position and the outer sheath member in a distal position relative to the pincher members;

FIG. 9 is a side elevational view in partial section of a portion of the hemostatic device constructed in accordance with the second embodiment of the invention, shown with the puncture site of the arterial lumen between a pair of biocompatible, bioabsorbable sleeves on the pair of pincher members to effect mechanical hemostasis and shown with a fibrin glue surrounding the puncture site;

FIG. 10 is a side elevational view in partial section of a portion of the hemostatic device constructed in accordance with a second embodiment of the invention, shown with the pair of pincher members in a partially retracted position from the puncture site and the biocompatible, bioabsorbable sleeves thereof separated therefrom and held adjacent the sealed puncture site with the fibrin glue which surrounds the puncture site; and FIG. 11 is a side elevational view in partial section of a portion of the hemostatic device constructed in accordance with a third embodiment of the invention, shown with the puncture site of the arterial lumen held between a pair of biocompatible, bioabsorbable sleeves on the pair of pincher members to effect mechanical hemostasis and shown with a thermoplastic sealant surrounding the puncture site;

FIG. 12 is a partial sectional view of a device constructed in accordance with a third embodiment of the present invention, shown with the locating device extended from the distal end portion of the delivery structure and inserted through the puncture and into the arterial lumen;

FIG. 13 is a partial sectional view of the device of FIG. 12 with the locating device retracted into the delivery structure, the outer sheath retracted to allow the distal end portion of the puncture site engaging member to expand, and a quantity of thrombogenic material delivered to the puncture site;

FIG. 14 is a partial sectional view showing the locating device used in the embodiment of FIG. 12 in isolation from the remaining components of the device.

DETAILED DESCRIPTION OF THE INVENTION

Figure 1:
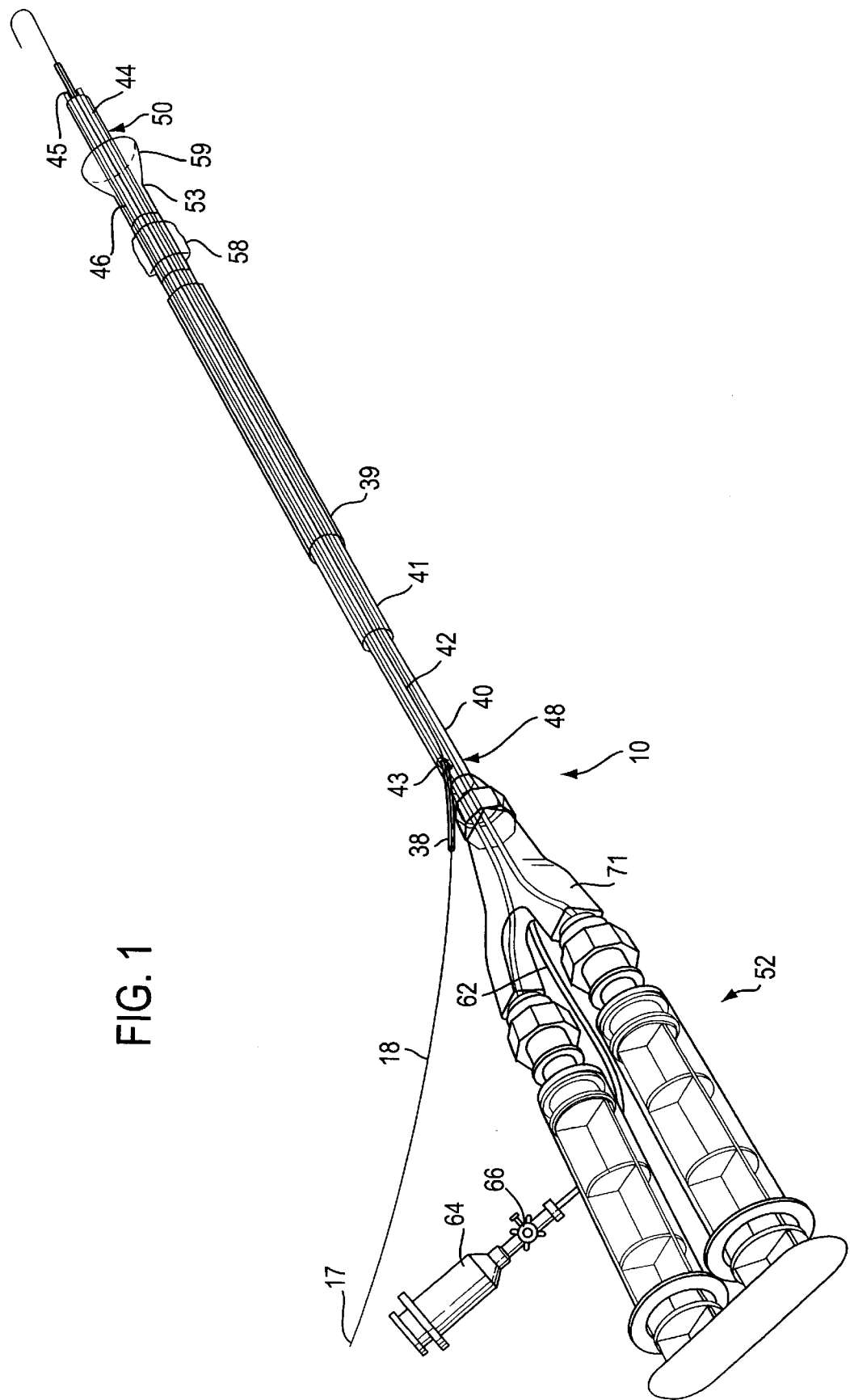
FIG. 1 is an isolated perspective view of a hemostatic device for sealing a subcutaneous puncture site provided in accordance with a first embodiment of the present invention.

FIG. 1 shows a device, generally indicated at 10, which embodies the principles of the present invention. The device 10 may be utilized for affecting hemostasis and closure of a puncture site or other type of opening in a blood vessel, duct or lumen within a living being. This device has particular utility when used in connection with intravascular procedures such as angiography, balloon angioplasty, intraaortic balloon pumping and other types of percutaneous intravascular or intracardiac interventions. A brief description of a conventional percutaneous transcatheter cardiovascular procedure, e.g., coronary angiography, percutaneous transluminal angioplasty, is given with reference to FIG. 3, to best appreciate the features of the present invention.

In a conventional procedure, an angiographic needle such as a Seldinger or Argon needle (not shown) is inserted percutaneously, through the skin 12, into an artery, such as the femoral artery 14. The angiographic needle with its tip disposed within the arterial lumen 16 is held while the flexible end of an angiographic guide wire 18 is advanced through the needle into the arterial lumen 16. Once the guide wire 18 is felt to be easily movable within the arterial lumen 16, the angiographic needle is withdrawn leaving the guide wire 18 in place. A conventional arterial dilator (not shown) and an arterial sheath (not shown) are threaded over the proximal end 17 of the guide wire 18 and advanced over the guide wire through the skin 12 and arterial wall into the arterial lumen 16. The guide wire 18 and dilator are then removed leaving the arterial sheath in place. Angiographic catheters or other intraluminal devices (not shown) are then passed through the arterial sheath and advanced within the artery 14 to the target site by passage over the guide wire. Once the angiographic or angioplastic procedure is completed, the catheters and guide wire 18 are removed, leaving the arterial sheath in place. Finally, the arterial sheath is removed, which then conventionally requires the physician or other trained medical personnel to apply manual pressure to the puncture site 24 until hemostasis has been achieved.

The device 10 and the method of the present invention produce hemostasis and closure of arterial puncture site 24 percutaneously, without necessitating prolonged manual arterial compression.

In accordance with the invention, hemostasis is effected by delivering a thrombogenic, hemostatic material to the puncture site 24 to promote clotting at the site. The thrombogenic, hemostatic material may include many bioabsorbable and biocompatible materials such as gelatin, blood and tissue components including collagen, blood coagulation factors, blood proteins, fibrinogens, fibrin, thrombin, epsilon aminocaproic acid, autologous blood clots and subcutaneous tissue, and other similar materials which will promote blood clotting when delivered to the puncture site. The thrombogenic, hemostatic material may also include a fibrin glue, generally indicated by the reference numeral 22 (FIGS. 5, 6, 9, and 10), or a thermoplastic sealant, generally indicated by the reference numeral 21 (FIG. 11).

When a fibrin glue 22 is the thrombogenic, hemostatic material used, the fibrin glue is typically produced by the admixture of two solutions, the first of which contains sodium citrate and autologous patient blood and the second of which contains bovine thrombin and aminocaproic acid in water. Preferably, the fibrin glue 22 is produced by the admixture of the following two solutions: the first solution contains fibrinogen and the second solution contains thrombin. Although it is preferred to mix two solutions together at the delivery site, a single thromobogenic, hemostatic material may be delivered to the puncture site. Further, two solutions may be used and delivered via a single delivery port or tube thereby mixing inside the delivery tube before reaching the site. This arrangement is not preferred because of the tendency for some materials to solidify inside the tube; however, it is within the scope of the present invention to use such an arrangement.

It can be appreciated that when a fibrin glue is used to effect closure of the puncture site 24, the fibrin glue 22 can be delivered to the puncture site 24 in various manners. For example, when the fibrin glue 22 is used to cover the puncture site 24, the two solutions which comprise the fibrin glue may be mixed remote from the puncture site 24 and then be delivered to the puncture site. Thus, the pre-mixed fibrin glue 22 can be delivered, for example, on the end of an elongated member and deposited at the puncture site 24, or the pre-mixed fibrin glue 22 can be delivered by injecting the fibrin glue from a tubular member once the tubular member is disposed at the puncture site 24. Another method of delivering the fibrin glue 22 to the puncture site 24 is to deliver the two solutions in separate ports to the puncture site 24 and thereafter intermix the two solutions to form the thrombogenic, hemostatic fibrin glue material 22. An advantage of this latter method which uses two separate ports to deliver the two solutions is that both solutions are in liquid form and have lower viscosity's than that of the fibrin glue, enabling them to flow easily to the puncture site. The fibrin glue 22 typically has a greater viscosity than the two liquid solutions, enabling the fibrin glue 22 to remain substantially in the deposited position, as will be more apparent below.

A delivery catheter is provided for delivering the thrombogenic, hemostatic material, which may be, for example, either a thermoplastic sealant 21 or a plurality of solutions which when mixed form a fibrin glue 22, to the puncture site 24. In addition to providing structure for delivering the material to the puncture site 24, the delivery catheter provides structure for applying mechanical hemostasis to the puncture site. The mechanical hemostasis at the puncture site 24 can be provided by a plurality of structures, including a blunt obturator, a pair of mechanical pinchers or a cone-like structure alone or in combination with a balloon.

Figure 2:
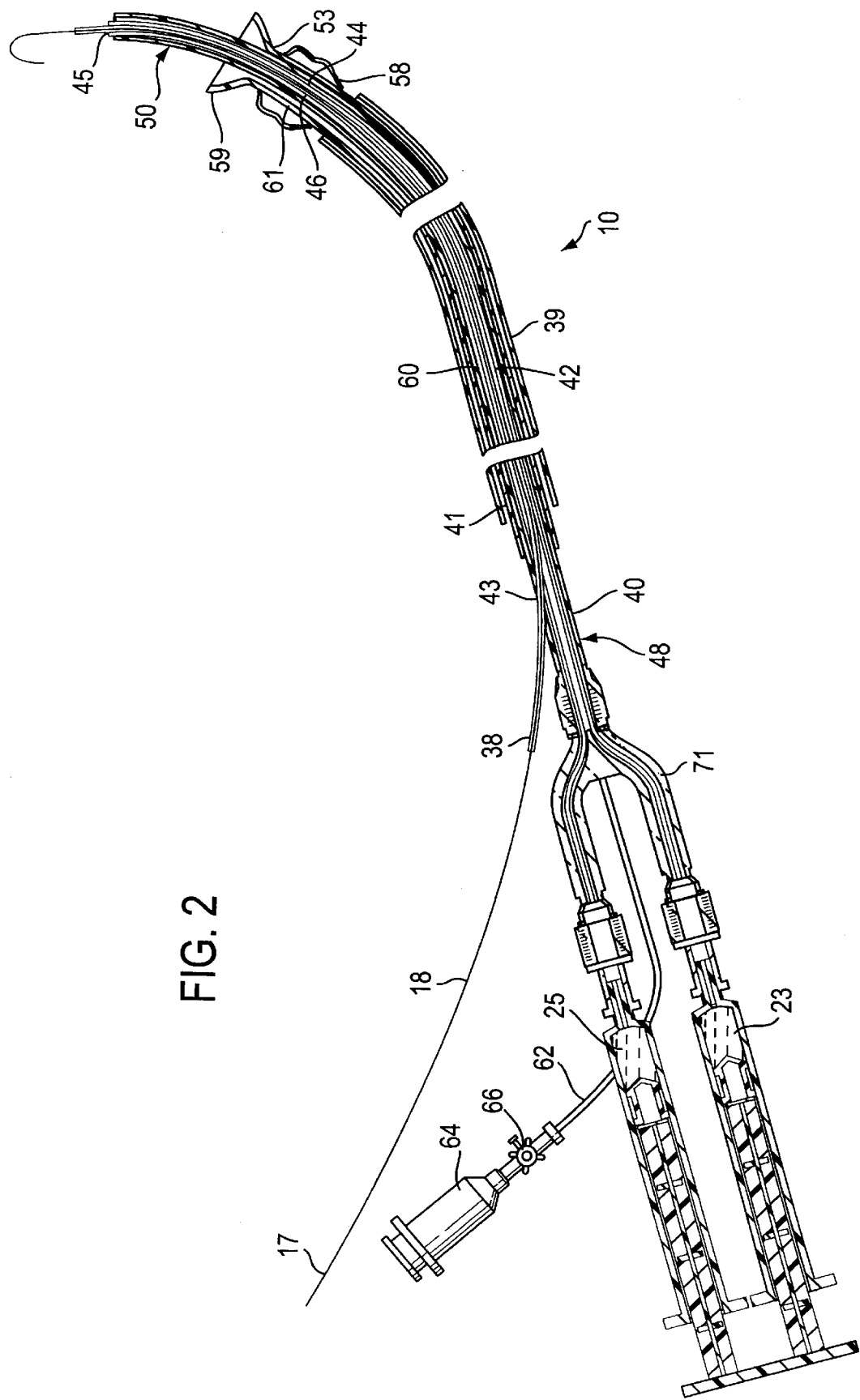
FIG. 2 is a side elevational view partially in cross-section of the hemostatic device of FIG. 1.

In a first embodiment of the invention as shown in FIGS. 1–6, a delivery catheter, generally designated 34, is provided for delivering a hemostatic, thrombogenic material to the puncture site 24. The delivery catheter includes a hollow outer sheath member 39, a hollow inner sheath member 41 defining a puncture site engaging member and a hollow tubular body member 40 comprising a part of delivery structure, which members 39, 40, 41 are best seen in FIG. 2. The tubular body member 40 and the inner and outer sheath members 39, 41 are preferably constructed of firm yet flexible material such as PET, polyvinyl chloride or the like. The inner sheath member 41 defining the puncture site engaging member is shorter than the tubular body member 40 defining the delivery structure and is slidably mounted between the tubular body member 40 and the outer sheath member 39; the outer sheath member 39 is shorter than the inner sheath member 41 and is, in turn, slidably mounted around the inner sheath member 41. Hence, the outer sheath member 39 and the inner sheath member 41 can independently slide longitudinally with respect to the tubular body member 40.

The tubular body member 40 comprising a part of the delivery structure includes a guide wire port 42 which extends from an opening 43 in the side of the tubular body member 40 along the longitudinal axis of the tubular body member 40 to a second opening 45 in the distal end of the tubular body member 40. A locating member in the form of a thin hollow tube 38 extends through and is slidably held within the guide wire port 42. The proximal end of the thin hollow tube 38 extends out of the opening 43 of the guide wire port 42 and the distal end portion of the thin hollow tube 38 (i.e., the locating member) extends out of the second opening 45 thereof. The thin hollow tube 38 is dimensioned to receive the guide wire 18 slidably therein. The tubular body member 40 of the delivery structure further includes a first solution delivery tube or port 44 and a second solution delivery tube port 46. Both ports 44, 46 extend along the longitudinal axis of the tubular body member 40 from a proximal end 48 thereof to a distal end 50 thereof and respectively define first and second fluid passageways therein. The body member 40, the ports 44, 46 and the fluid passageways formed therein may be considered together as the delivery structure. However, any means for delivery the fluid thromogenic material may be used as the aforementioned delivery structure. Each port 44, 46 is coupled to and in fluid communication with a syringe 52 at the proximal end thereof. The syringes 52 facilitate delivery of a first and a second solution, generally designated 23 and 25, respectively, to the puncture site 24 through appropriate solution delivery ports 44, 46 at the distal end of the tubular body member 40. The syringes 52 may also be considered part of the delivery structure.

As best seen in FIG. 2, a self-expanding cone shaped structure 59 is integrally formed at the distal end portion 53 of the inner sheath member 41 defining the puncture site engaging member. A low pressure balloon 58 is slidably affixed to the inner sheath member 41 proximal the cone shaped structure 59. The balloon 58 is affixed to the inner sheath member 41 by threads or the like. The balloon 58 is made of material similar to that of the elongated tubular body member 40 and may be of any well known configuration so that when inflated, the balloon 58 may define a wedge shape, a corrugated shape, an annular shape or the like. The inflated balloon 58 serves to exert lateral pressure outwardly against the surrounding subcutaneous tissue 32 and by so doing, secures the distal end 50 of the tubular body member 40 against the puncture site 24. The inner sheath member 41 and the integral cone shaped structure 59 are preferably made of a resilient, flexible material and can be made of the same material used to make the tubular body member 40.

Figure 3:
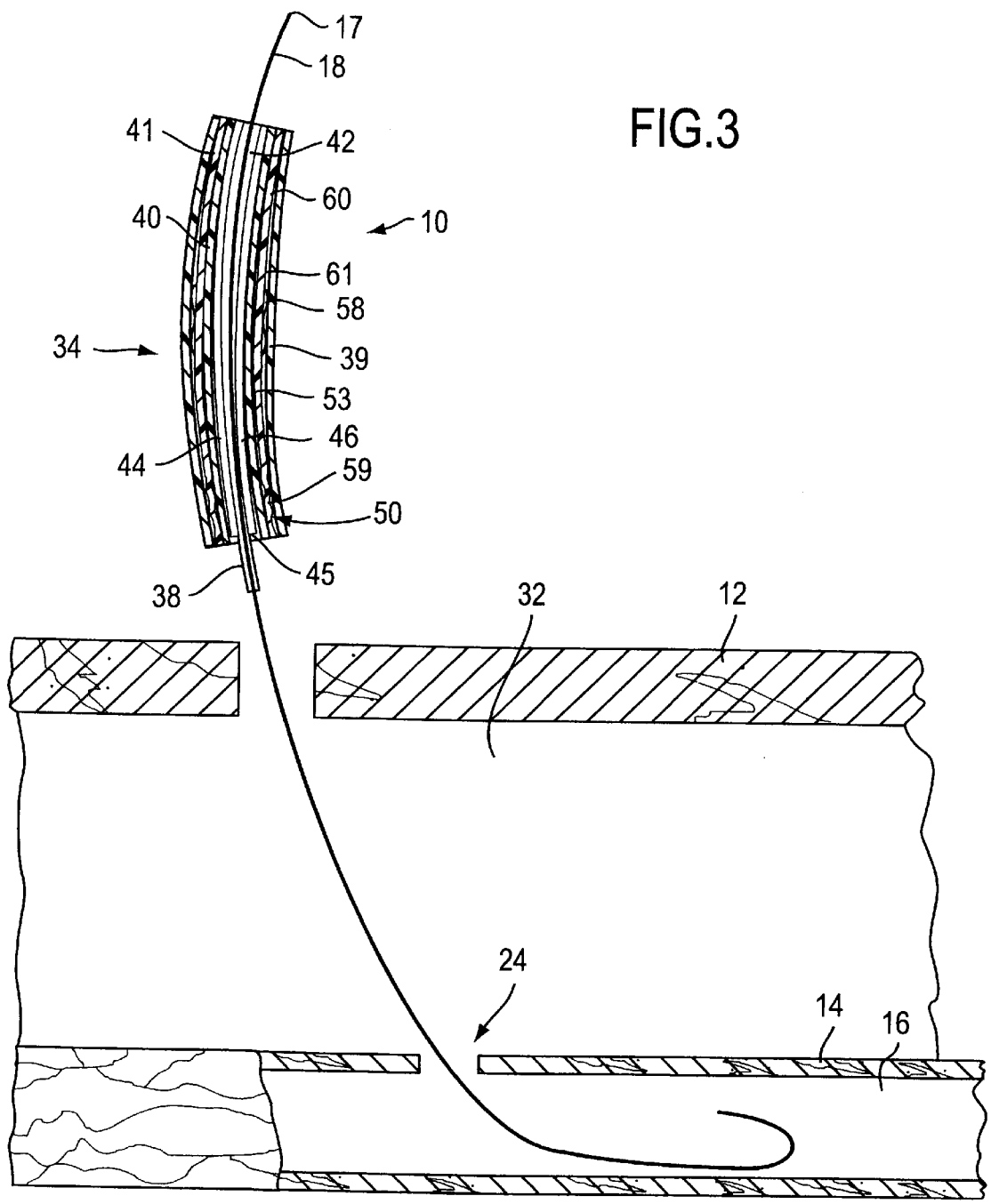
FIG. 3 is a side elevational view in partial section of a portion of the hemostatic device constructed in accordance with the first embodiment of the invention, about to be inserted through a percutaneous puncture into proximity with a puncture site in an arterial lumen.
Figure 4:
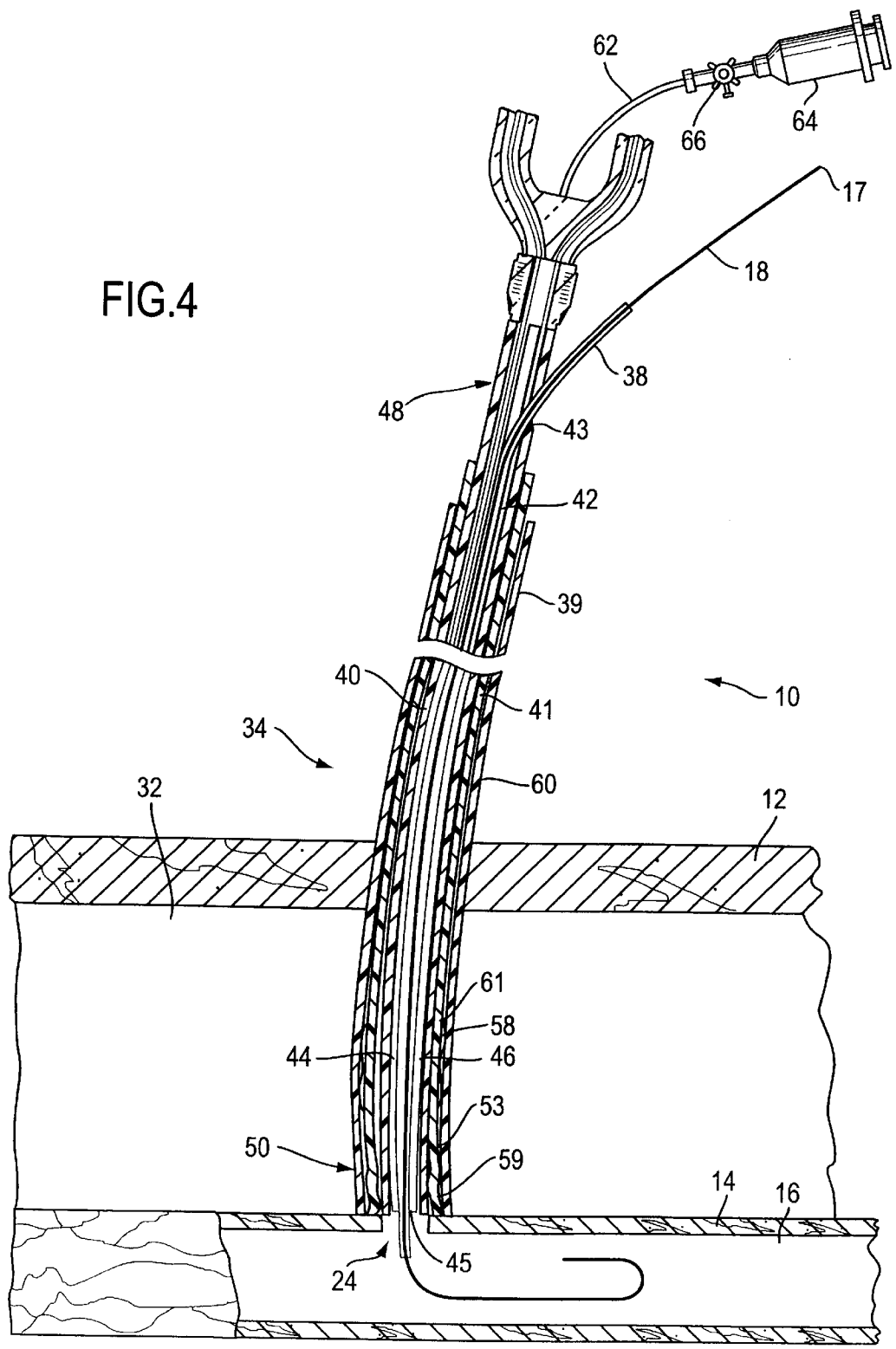
FIG. 4 is a side elevational view in partial section of a portion of the hemostatic device constructed in accordance with the first embodiment of the invention, shown with a locating member of the hemostatic device partially within the arterial lumen.
Figure 5:
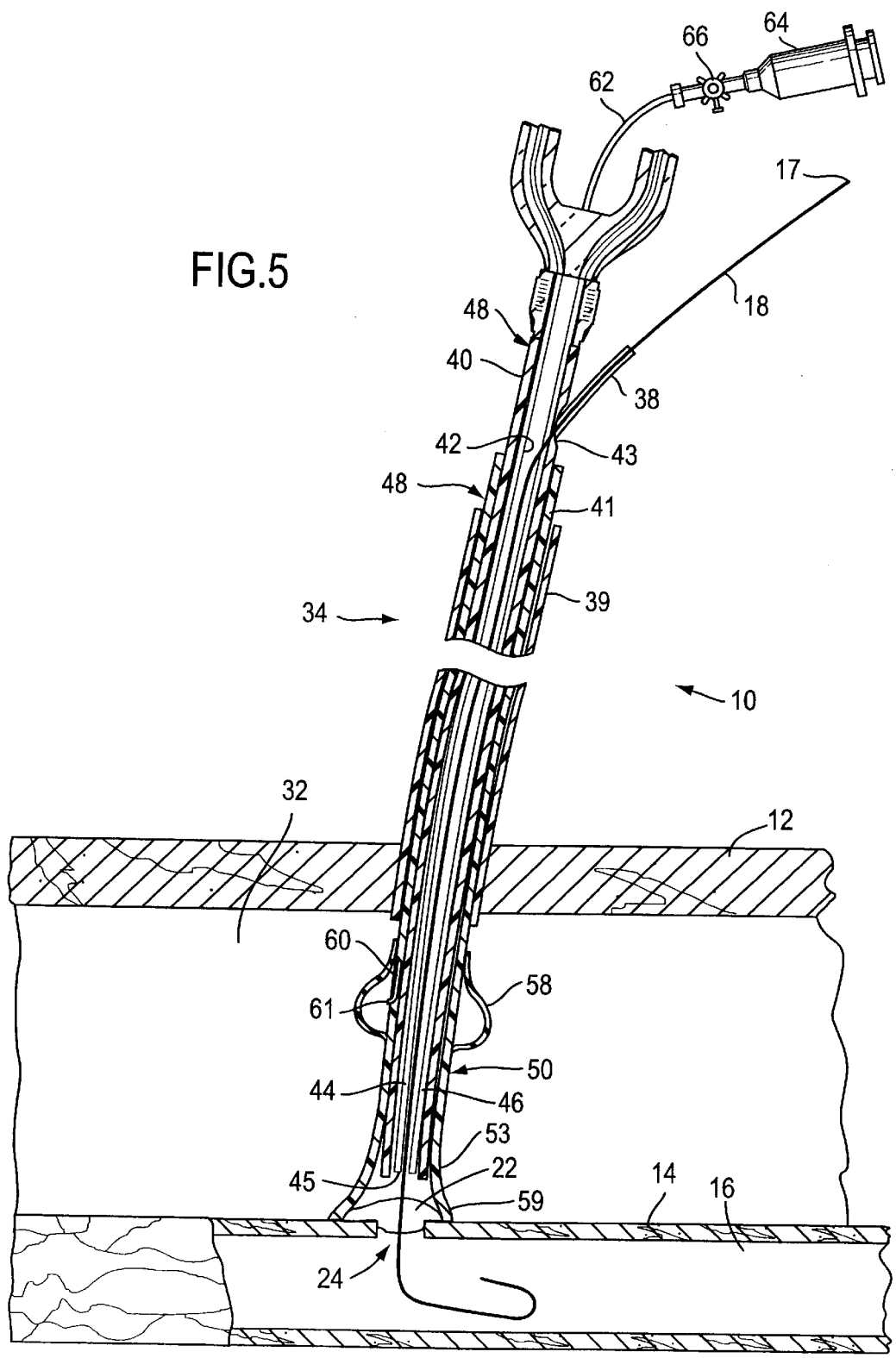
FIG. 5 is a side elevational view in partial section of a portion of the hemostatic device constructed in accordance with the first embodiment of the invention, shown with a cone shaped structure thereof in an open configuration over the puncture site in the arterial lumen which puncture site is sealed with a fibrin glue and shown with a balloon in an inflated configuration.

The cone shaped structure 59 is constructed such that it normally assumes the open, cone shaped configuration. As best seen in FIGS. 3 and 4, however, the cone shaped structure 59 can be resiliently deformed by folding or by radial compression into a closed configuration and contained within the outer sheath member 39 which maintains the cone shaped structure 59 in the closed configuration until the outer sheath member 39 is moved proximally with respect to the inner sheath member 41, thereby allowing the cone shaped structure 59 to resiliently expand and return to its cone shaped configuration. In the illustrated embodiment of the delivery catheter 34, the maximum outer diameter of the catheter 34 measured around the outer sheath member 39 is between 5 and 10 French inclusive, which enables the delivery catheter 34 to pass easily through the percutaneous opening to advance to the puncture site 24.

It should be understood that other elements may be used in place of the self-expanding cone-shaped structure 59. For example, the distal end portion 53 of the inner sheath or puncture site engaging member 41 may comprise a flexible material which will expand as the thrombogenic material is being delivered to the puncture site and filling up the interior space of the distal end portion 53. Such flexible material may be a thin plastic sheet wrapped around the distal end of the member 41.

A passage 60 extends longitudinally within a portion of the wall of the inner sheath member 41 and terminates in aperture 61. The passage 60 is provided for inflating the balloon 58. The passage 60 connects with a tube 62 which in turn is attached to an inflating syringe 64. A stopcock 66 is provided to regulate the inflation of the balloon 58. The passage 60 communicates pressurized ambient atmosphere or other fluids or gases to the balloon 58 when the balloon is positioned over the aperture 61.

A second embodiment 35 of the device 10 is shown in FIGS. 7–10. The device 10 is similar in many respects to that of the first embodiment. Accordingly, corresponding part numbers are assigned the same reference numbers and will not be specifically described unless necessary.

In this second embodiment 35, the guide wire port 42 extends the entire length of the tubular body member 40 of the delivery structure and is aligned with an identically dimensioned elongated port 69 formed in a portion of a syringe connector structure 71. The guide wire tube or port 42 and elongated tube or port 69 cooperate to form a single tube or port which slidably receives the thin hollow tube 38, which tube 38 in turn slidably receives the guide wire 18 therein. The thin hollow tube 38 is longer than the combined length of the port 69 and the port 42 so that the thin hollow tube 38 extends out of the proximal end of port 69 and the distal end of port 42 as shown in FIG. 7.

The tubular body member 40 shown in FIGS. 7–10 includes a pair of identical, opposing pincher members 86. Each pincher member 86 defines a plurality of portions formed integrally therewith, including an elongated upper portion 88, an outwardly directed lower portion 90, and straight end portions 92. Each pincher member 86 is preferably a resilient, flexible metal structure which can be resiliently deformed by a bending force and return to its original configuration after the bending force is removed. In the absence of a bending force, the pincher members 86 assume an open configuration in which the straight end portions 92 thereof are spaced apart. An example of this configuration is shown in FIG. 8. Each straight end portion 92 of each pincher member 86 is configured so that when the pincher members 86 are brought together, the straight end portions 92 are essentially parallel and side by side. Each straight end portion 92 is preferably surrounded by a removable sleeve member 94, each of which is comprised of a biocompatible, bioabsorbable material such as polyglycolate or polylactate. The elongated portion 88 of each pincher member 86 is secured within the tubular body member 40. The elongated portion 88 of each pincher member 86 may extend essentially the entire length of the tubular member 40 as shown in FIGS. 7–10, or, alternatively, the elongated portion 80 of each pincher member 86 may extend only a short distance into the distal end of the tubular body member 40.

This second embodiment of the device 10 includes an outer sheath member 39 which is slidably mounted around the tubular body member 40, but the device 10 does not include an inner sheath member 41. In this second embodiment, the outer sheath member serves as the puncture site engaging member.

A third embodiment 37 of the device 10 is shown in FIG. 11. This third embodiment 37 of the device 10 is similar in many respects to that of the first and second embodiments 34, 35. Accordingly, corresponding part numbers are assigned the same reference numbers and may not be specifically described unless necessary.

It can be appreciated from FIG. 11 that the device 10 may seal the puncture site 24 by deploying a hemostatic, thrombogenic thermoplastic sealant 21 using the combination of the heated sealant 21 and pressure, optionally followed by rapid cooling of the sealant 21 and the surgical site. The combination of heat and pressure has been shown to be effective in fusing vascular tissues together.

In this third embodiment, a sheath member 68 is slidably disposed around the tubular body member 40 and serves as the puncture site engaging member.

The sheath member 68 includes an element for heating the distal end portion thereof. The distal end portion 72 of the sheath member 68 preferably includes an outer Teflon layer 74, a mid-layer 76 of stainless steel and an inner conductive layer 78 made of copper or other conductive material. The conductive layer 78 is electrically connected to a plurality of wires 80. The wires 80 are connected in a conventional manner to a power source (not shown). A quantity of thermoplastic sealant 21 in a ring-shaped configuration is secured to the interior of the sheath member 68 and is in contact with the inner conductive layer 78 thereof. Any conventional thermoplastic sealant can be used in the device 10 including polylactates. The conductive layer 78 can be heated by passing energy through the wires 80 from a variety of power sources, such as alternating current, direct current, RF or microwave energy. This heating melts the thermoplastic sealant. Two infusion channels 82, 84 which extend the length of the catheter body may be included in the tubular body member 40 to allow the passage of coolant to and from the distal tip 77 of the sheath member 68, which coolant acts to cool the tip of the sheath member 68, the thermoplastic sealant and the adjacent living tissue quickly. Alternatively, the first solution delivery port 44 and the second solution delivery port 46 may be used to circulate coolant to and from the distal tip. The manner in which this sheath member 68 and the thermoplastic sealant therein is used to close a subcutaneous puncture wound will be considered fully when the operation of the third embodiment of the device 10 is discussed.

FIGS. 12–14 illustrate a device 100 constructed in accordance with a fourth embodiment of the present invention. The device 100 is similar in many respects to the device of the first embodiment (FIGS. 1–6). Thus, the same references numerals will be used to denote identical or similar structures and detailed descriptions of such structures shall be omitted as they have already been described.

The device 100, like the device 10 of the first embodiment has a delivery catheter 102 comprising the retractable outer sheath 39, the inner sheath member 41 (i.e., the puncture site engaging member) with the expanding cone structure 59 on the distal end portion 53 thereof, and the guide wire 18. In place of the tubular body member 40, a tubular body member 104 with a self-closing tip 106 is provided. The body member 40 has a pair of ports 108 and 110 open to the distal end portion thereof and connected to the fluid passageways defined by ports or tubes 44 and 46, respectively. As in the first embodiment, tubes or ports 44 and 46 are communicated to the first and second solution supplies (not shown) and these solutions and delivered to the puncture site 24 through the fluid passageways defined by tubes or ports 44, 46 and outwardly from ports 108 and 110.

The self-closing tip 106 is constructed from a resiliently deformable material and may be formed integrally with the delivery structure 104 or be attached to the distal end thereof as a separate component. The tip 106 has a normally closed configuration, as best seen in FIG. 13, in which the material defining the tip 106 is resiliently collapsed inwardly upon itself to close the aperture 112 formed therein. As shown in FIG. 12, a locating device in the form of a blunt-tipped obturator 114 can be forced through the aperture 112 so as to resiliently deform the material defining the tip 106 outwardly and expand the aperture 112. Preferably, the tip 106 is constructed such that the aperture 112 is substantially sealed when the tip 106 assumes its normally closed configuration.

The blunt-tipped obturator has a tubular, hollow configuration and is movable along the guide wire 18 relative to the other components. Specifically, the obturator has a cone-shaped distal end portion 116 with an aperture 118 formed therethrough through which the guide wire 18 is received. The obturator 114 has two ports 120, 122 formed through the wall thereof and spaced apart in the longitudinal direction of the obturator 114. A pair of thin hollow tubes 124, 126 are connected to these ports 120, 122, respectively, and open to the exterior of the obturator 114. These tubes 124, 126 extend proximally away from the distal end portion 116 of the obturator.

OPERATION

The device can be used in a plurality of ways to seal a subcutaneous puncture. Examples of several methods for sealing a puncture in a femoral artery 14 using an embodiment of the device 10 are shown in the drawings. A first example of a procedure for placing a fibrin glue 22 at the puncture site 24 using the delivery catheter 34 to close the puncture can be appreciated with reference to FIGS. 3–6. Upon completion of the catheterization procedure and following the removal of the catheters required therefor, and with the arterial sheath remaining in place, the guide wire 18 is passed through the arterial sheath into the arterial lumen 16. The arterial sheath is then completely withdrawn from the patient leaving only the guide wire 18 in the arterial lumen 16. The guide wire 18 is constructed in a conventional manner and is generally comprised of a single stainless steel cylindrical core wire surrounded by a single stainless steel cylindrical peripheral wire wrapped spirally thereabout. The surgeon can change the configuration of the distal tip of the guide wire 18 to effect the configurations shown, for example, in FIGS. 3 and 7. It can be appreciated that the tip of the guide wire 18 can be reconfigured by the surgeon in a conventional manner so that the tip can be varied between an essentially linear configuration to a hook shaped configuration shown in FIG. 3.

The distal end of the thin hollow tube 38 defining the locating device slidably disposed within the hemostatic catheter 34 is then threaded onto the proximal end of the guide wire 18. The delivery catheter 34 is then advanced toward the puncture site 24. It can be appreciated from FIG. 3 that as the delivery catheter 34 enters through the patient's skin 12, the balloon 58 on the inner sheath member 41 is fully deflated and the outer sheath member 39 surrounds both the balloon 58 and the cone shaped structure 59. Thus, the cone shaped structure 59 on the inner sheath member 41 is enclosed within the outer sheath member 39 and this holds the cone shaped structure 59 in a resiliently closed configuration. It should be noted, however, that the outer sheath member 39 will be omitted when the distal end portion 53 is made of a flexible material, such as a thin plastic film, that expands as a result of the fluid thrombogenic material being delivered to the puncture site 24. This is because the distal end portion is not self-expanding in this arrangement and thus does not need to be restrained.

In this configuration, the delivery catheter 34 can be advanced along the guide wire 18 into and through the skin 12 and subcutaneous tissue toward the puncture site 24. Brief manual pressure may be exerted on the artery 14 from the time the arterial sheath is withdrawn from the patient until the distal tip of the delivery catheter 34 is disposed against the arterial wall 14. The surgeon is able to determine easily when the delivery catheter 34 is against the arterial wall 14 because of the thin hollow tube 38. It can be appreciated from FIG. 3 that as the delivery catheter 34 approaches the puncture site 24, the thin hollow tube 38 extends slightly out of the distal end of the delivery catheter 34. In this configuration, the thin hollow tube 38 will be the first portion of the delivery catheter 34 to enter the puncture site 24. This is important because once the thin hollow tube 38 has penetrated the puncture site 24 and is within the arterial lumen 16, the small diameter thin hollow tube 38 transports blood proximally therethrough and toward the proximal end of the thin hollow tube 38. The blood is carried proximally by both the capillary action of the thin hollow tube 38 and by the fluid pressure of the pulsating blood in the artery. Thus, the proper position of the device 10 relative to the arterial puncture site 24 is indicated by the presence of blood within the thin hollow tube 38. It should be noted that in restricted blood flow situations or when the device is locating the tissue wall of a cavity containing nonflowing fluids, a vacuum may be used to cause the proximal fluid flow.

It can be appreciated from the Figures that the proper positioning of the distal end portion of the catheter 34 is achieved as a result of the catheter 34 being positioned relative to the thin hollow tube 38 (i.e., the locating device) such that, when the tube 38 has entered the artery and the flow of blood is communicated to the interior of the tube 38, the distal end portion of the catheter 34 will be engaged with the exterior of the artery. In particular, it is most desirable that at least the inner sheath member 41 be engaged with the artery exterior. The relative positioning of the outer sheath member 34 and the body member 40 are of less importance, although it is preferred that their positions be also dictated by the positioning of the thin hollow tube 38.

Once the delivery catheter 34 including the outer sheath member 39, inner sheath member 41 and the tubular body member 40 have advanced to the vessel 14, the delivery catheter 34 is secured adjacent the puncture site 24 by either manual pressure or the balloon 58. This is accomplished by sliding the outer sheath member 39 proximally which allows the cone shaped structure 59 to expand. This expansion of the cone shaped structure 59 compresses the adjacent subcutaneous tissue and holds the inner sheath member 41 and the tubular body member 40 against the puncture site 24 to secure the delivery catheter 34 adjacent the puncture site 24. If the surgeon desires, the balloon 58 on the inner sheath member 39 can also be inflated using the inflation syringe 66. This would further compress the subcutaneous tissue and hold the delivery catheter 34 more firmly adjacent the puncture site 24. It should be noted that the balloon 58 is considered unnecessary and the catheter may be manually pressed against the puncture site.

The thin hollow tube 38 is then withdrawn from the artery 14 and from the delivery catheter 34, respectively, and the distal tip of the tubular member 40 is engaged directly against the arterial puncture site 24. The two solutions 23, 25 which comprise the fibrin glue 22 are then delivered through ports 44 and 46, respectively, to the puncture site 24 and mixed within the cone shaped structure 59 to form the fibrin glue 22. The cone shaped structure 59 allows the fibrin glue 22 to become firm within a confined space and prevents the glue from flowing away from the puncture site before hardening. Because the fibrin glue 22 has a relatively high viscosity, the fibrin glue 22 remains contained between the cone shaped structure 59 and the puncture site 24. Hence, the cone shaped structure 59 makes it possible to apply the fibrin glue 22 to the puncture site 24 without dispersing the fibrin glue 22. Manual pressure may be applied to assist with hemostasis until the fibrin glue hardens. The conical shape of the interior of the cone shaped structure 59 causes the fibrin glue 22 to harden in a configuration that closely resembles the natural configuration formed by coagulated blood in sealing wound.

The cone shaped structure 59 and the optionally inflated balloon 58 stabilizes the mechanical pressure against the puncture site 24 and permits full patient ambulation while the delivery catheter 34 remains in place. When the fibrin glue 22 is sufficiently set, the guide wire 18 can be withdrawn. Once hemostasis is achieved, the balloon 58 is deflated (if it has been used) and the cone shaped structure 59 is enclosed once again within the outer sheath member 39 and the delivery catheter 34 is removed from the patient. When the delivery catheter 34 is removed from the patient, the fibrin sealant is left as a mound over the puncture site 24.

The device 10 may seal a puncture site 24 by using pincher members 86 in combination with the fibrin glue 22 as shown in FIGS. 7–10. When this embodiment is used, after the surgical procedure is completed with the guide wire 18 still in place within the arterial lumen 16, the arterial sheath is completely removed from the patient. The proximal end of the guide wire 18 is threaded through the distal end of the thin hollow tube 38 of the device 10. As best seen in FIG. 7, as the device advances along the guide wire 18 toward the puncture site 24, a distal portion of the outer sheath member 39 of the device 10 surrounds the pincher members 86 and holds them resiliently closed. The thin hollow tube 38 may be held therebetween as shown in FIG. 7. The device 10 is advanced until the presence of blood in the thin hollow tube 38 indicates that the device 10 has achieved the proper position relative to the puncture site 24.

Manual pressure surrounding the puncture site 24 provides mechanical hemostasis while sealing takes place. The outer sheath member 39 is then moved proximally with respect to the tubular body member 40 which allows the pincher members 86 to expand outwardly to the open position. This open position of the pincher members 86 effected by the proximal movement of the outer sheath member 39 is shown in FIG. 8. The pincher members 86 are then pressed downwardly against the puncture site 24 in the vessel 14 with light pressure while the outer sheath member 39 is moved distally which brings the pincher members 86 together. This causes the punctured site 24 to be pinched shut between the biocompatible, bioabsorbable, removable sleeves in the pincher members 86. This results in highly effective mechanical hemostasis which can be maintained while a chemical hemostatic, thrombogenic agent is introduced.

The outer sheath member 39 is advanced over the pincher members 86 until the outer sheath member 39 contacts the vessel arterial lumen wall 14. The outer sheath member 39 therefore surrounds the puncture site 24 forming an enclosure or reservoir to contain a hemostatic, thrombogenic chemical substance and hold the same in contact with the puncture site 24 until hemostasis is achieved. The puncture site 24 can be sealed, for example, by a fibrin glue 22, as shown in FIG. 9. The fibrin glue 22 is introduced through the first solution delivery port 44 and the second solution delivery port 46, each of which ports 42, 44 is in fluid communication with a syringe 52 which contains a component of the fibrin glue 22. When the fibrin glue 22 is used, the puncture site 24 is pinched together by the pincher members 86 until the site 24 is sealed. Once adequate sealing takes place, the guide wire 18 and the hollow tube 38 are removed. A second dose of sealant can then be used to optimize sealing. Then the pincher members 86 are withdrawn leaving the bioabsorbable, biocompatible sleeves behind as part of the plug formed by the fibrin glue 22. The device 10 can then be withdrawn from the patient. It can be appreciated that once the puncture site 24 is pressed between the pincher members 86 which effectively hold the puncture site 24 closed, the patient it capable of ambulation.

The third embodiment 37 of the device 10 is shown in FIG. 11. This third embodiment is similar in many respects to the first embodiment 34 shown in FIGS. 1–6 and to the second embodiment 35 shown in FIGS. 7–10. Accordingly, corresponding structures are assigned the same reference numbers and may not be specifically described.

The manner in which the third embodiment of the device 10 is used to seal a puncture site 24 is shown in FIG. 11. The sheath member 68 of this third embodiment is capable of applying a hemostatic, thrombogenic thermoplastic sealant 21 to the puncture site 24 while the punctured portion of the vessel 14 is held between the removable bioabsorbable, biocompatible sleeves. The device is advanced to the puncture site 24 in the same way as above described when discussing the second embodiment of the device 10. Hence, after the arterial sheath is removed and with the guide wire 18 still in place within the arterial lumen 16, the proximal end of the guide wire 18 is inserted in the distal end of the thin hollow tube 38 of the third embodiment and the device 10 is advanced toward the puncture site 24 with the pincher members 86 held together by the sheath member 68 until the presence of blood in the thin hollow tube 38 indicates that the device is in a proper position relative to the puncture site 24. The sheath member 68 is then moved proximally to open the pincher members 86 and then distally to close them so that the puncture site 24 is held between the sleeves.

It can be appreciated that once the puncture site 24 is held together by the sleeves on the pincher members 86, the sheath member 68 can be advanced distally until it is in contact with the vessel 14. Energy can then be delivered to the conductive layer 78 through the wires 80 to heat the sealant 21. As the temperature of the sealant 21 increases, the sealant 21 flows to the puncture site 24 to achieve hemostasis. When the sealant is in place around the puncture site 24, a coolant can be circulated to and away from the puncture site 24 through fusion channels 82, 84. Thereafter, the pincher members 86 can be withdrawn leaving the sleeves embedded in the hardened sealant 21. It can be appreciated that once the pincher members 86 of the third embodiment pinch the puncture site 24 closed, the patient is capable of ambulation.

Referring to the fourth embodiment and FIGS. 12–14, the operation of that embodiment will be discussed. Similarly to the first three embodiments, the catheter 102 is slidably mounted on the guide wire 18 and advanced towards the puncture site 102. Specifically, the obturator 114 is extended distally to its extended, operative position (as shown in FIG. 12) and the aperture 118 on the obturator 114 is slidably mounted over the guide wire 18. In this position, both ports 120, 122 are disposed outside the self-closing tip 106 of the delivery structure 104.

The diameter of the obturator 114 is selected to substantially fill in or occlude the puncture as the catheter 102 is moved forwardly (distally) along the wire 18. Specifically, when the obturator 114 is received within the puncture, it substantially occludes the puncture to prevent blood from flowing out through puncture.

The two ports 120, 122 play an advantageous role in the operation of the present invention. The tubes 124, 126 connected to these ports 120, 122 function in substantially the same way as hollow tube 38 of the first three embodiments. In particular, when either of these ports 120, 122 is positioned inside the artery, blood will flow up through the respective tubes 124, 126 to a point to where the physician can visually verify that the particular port is located inside the artery. The visual verification can be either through transparent sections of the tubes 124, 126 or through blood being allowed to flow out the proximal ends of the tubes 124, 126. The positioning of the two ports 120, 122 is selected so that the body of the obturator 114 will substantially occlude the puncture when at least one of the ports 120, 122 is positioned inside the blood vessel.

Before movement towards the puncture site 24, the obturator 114 is positioned with respect to the catheter (and the inner sheath member 41 defining the puncture site engaging member) such that the distal end portion 53 of the inner sheath member 41 will be engaged with the exterior of the artery in surrounding relation to the puncture site 24 when the distal one of the ports 122 is positioned inside the artery interior so as to allow blood to flow proximally through tube 126, and the proximal one of the ports 120 is positioned outside of the artery interior. In the embodiment illustrated, the vessel wall 14 is shown as being located between the two ports 120, 122. However, it is contemplated that the proximal port 120 could be located in line with the vessel wall, or even partially in the interior, as long as the blood does not flow up the tube 124 to signal the physician.

It should be noted that other arrangements could be used in place of the obturator 114 could be used to effectively position the device 100. For example, the distal and proximal ports could be provided by staggering two thin hollow tubes similar to tube 38 longitudinally along the guide wire 18. In this arrangement the opening (port) of one tube would be inside the blood vessel and the opening (port) of the other tube would be outside the blood vessel when proper positioning has been achieved.

At this point, the obturator 114 is occluding the puncture and the inner sheath member 41 is in proper position. The outer sheath member 39 is then withdrawn to allow the self-expanding cone structure of the distal end portion 53 to expand. As mentioned above with respect to the first embodiment, the outer sheath member 39 may be omitted and the cone structure 59 does not have to be of the self-expanding type.

With the obturator 114 occluding the puncture and the distal end portion 53 of the inner sheath member 41 engaging vessel exterior in surrounding relation to the puncture, the fluid thromogenic material, preferably fibrin glue 22, will be delivered through the ports 108 and 110 and deposited on the vessel exterior around the puncture and the obturator 114. The obturator 114 can then be withdrawn from the vessel interior and into the body of the delivery structure 104. The self-closing tip will then self-close and the thromogenic material will continue to be delivered to the puncture site so as to fill in any hole left behind by the removal of the obturator 114. The closed self-closing tip 106 of the delivery structure 104 can then be used to compress and flatten the fibrin glue 22 against the puncture site 24 by moving the body member forwardly (distally) relative to the guide wire 18 and sheath member 41. After the fibrin glue 22 has sufficiently hardened, the wire 18 and the catheter 102 may then be withdrawn from the patient.

It can be appreciated by one skilled in the art that it is within the scope of the invention to vary the device 10. Many variations of the first embodiment of the device 10 shown in FIGS. 1–6, for example, are contemplated by the present inventor. For example, the first embodiment of the device 10 can be modified by not including the outer sheath member 39 and the balloon 58. In this variation of the first embodiment of the device 10, the cone shaped structure 59 could be folded manually by the surgeon immediately prior to the insertion of the structure 59 through the skin 12. The cone shaped structure 59 would then be advanced along the guide wire 18 to the puncture site 24 to seal the same. Also, as mentioned before, the cone-shaped structure could be omitted and a flexible plastic film could be wrapped around the distal end of the member 41.

The first embodiment of the device 10 (and the fourth embodiment 100) can be modified to provide a device 10 without an outer sheath member 39 and without a balloon 58 which device would include a pneumatically inflatable cone shaped structure 59. In this variation of the device 10, the inner sheath member 41 and the cone shaped structure 59 integrally formed thereon are modified to include a small lumen in the wall of the inner sheath member 41 and at least one inflatable chamber in the cone shaped structure 59. The inflatable chamber in the cone shaped structure 59 is in fluid communication with the lumen in the wall of the inner sheath member 41 and the lumen is, in turn, in fluid communication with a fluid source which fluid source can provide a fluid to inflate the chamber in the cone shaped structure 59. The fluid could be, for example, compressed gas from the ambient atmosphere provided by an inflation syringe which could be a fluid source in a conventional manner. The chamber in the cone shaped structure 59 could assume many shapes and configurations. The chamber could, for example, be an annular structure formed around the distal end of the cone shaped structure 59. It can be appreciated that when the cone shaped structure 59 is made inflatable by the inclusion of an inflation chamber, the cone shaped structure 59 would not be made of a resiliently flexible material that retains a specific shape, but rather would be constructed of a softer material such as might be used to construct a balloon 58 which would be soft an pliable in an uninflated state. The cone shaped structure 59 would be advanced to the puncture site 24 in the this pliable uninflated state and then inflated into a turgid conical configuration.

One variation on the fourth embodiment of the device 100 is to make the diameter of the obturator 114 variable so that it can fit into and substantially occlude punctures of varying sizes. Specifically, it is contemplated to communicate the interior of the obturator 114 to a low pressure air source so that the obturator 114 can be inflated or deflated to vary its diameter.

It is within the scope of the invention to provide all of the above embodiments of the device 10 as disposable units delivered to the surgeon in a hermetically sealed, sterile package. The device 10 may be provided in the sealed package to the surgeon with or without a guide wire 18 in place within the thin hollow tube 38 of the device 10. Similarly, the device 10 may be provided in the sealed package with the solutions required to make the fibrin glue 22 already contained within the syringes 52 which are part of the device 10. It is also within the scope of the invention to provide the device 10 pre-packaged with other thrombogenic, hemostatic materials or other medicaments useful in sealing a puncture or hole in a lumen.

It is also within the scope of the invention to provide a single port such as port 44 within the tubular body member 40 of the delivery catheter 34 for delivering pre-mixed fibrin glue 22 to the puncture site 24. This could be accomplished, for example, by directing the solutions 23, injected from the syringes 52 into a common port in the distal end of the syringe connector structure 71 which common port is in fluid communication with single port in the tubular body member 40. It can be appreciated that the solutions 23,premix in the common port in the connector structure 71 and are delivered to the puncture site 24 as a fibrin glue 22.

The pincher members 86 on the device 10 need not include sleeves and the distal ends pincher members 86 need not assume an essentially parallel configuration when the pincher members 86 are brought together. The distal ends of the pincher members 86, for example, may be angled inwardly so that when the pincher members 86 are brought together, only the distal tips of the distal ends are in contact.

It can be appreciated that the method of the present invention provides hemostatic closure of a puncture site or other opening in other types of ducts or lumina within the body without obstructing blood flow.

Thus, it is to be understood that while the description of the invention as contained herein is directed to closure of percutaneous punctures in arteries, the device and method have wide-spread applications. It can be appreciated by those skilled in the art that while the invention may have primary utility for the percutaneous hemostatic closure of arterial punctures following percutaneous transluminal intravascular procedures, the invention also facilitates percutaneous closure of punctures or openings in any organ, wall or tissue plane separating separate lumina or cavities in a living being.

It has thus been seen that the objects of this invention have been full and effectively accomplished. It will be realized, however, that the foregoing preferred embodiments have been shown and described for the purposes of illustrating the structural and functional principles of the present invention, as well as illustrating the method of employing the preferred embodiments and are subject to change without departing from such principles.

Any U.S. Patents and patent applications mentioned hereinabove and not specifically incorporated into the present application by reference are hereby incorporated by reference into the present application, including those patents cited in the introductory section of the present application.

It should be noted that the appended claims do not include language in the "means or step for performing a specific function" format permitted by 35 U.S.C. § 112, paragraph 6. Thus, it is intended that the appended claims not be interpreted as being limited to the structures, material, or acts described in the present application.

What I claim:

1. A device for percutaneously sealing of an internal puncture site comprising a tissue portion having a puncture formed therethrough, the puncture site being accessible through a perforation formed through the skin and subcutaneous tissue of a living being with an elongated guide wire being inserted through the perforation and into the puncture, said device comprising:

a locating device constructed and arranged to be mounted for longitudinal movement relative to said guide wire towards and away from the puncture site;

a supply of fluid thrombogenic material which will be capable of promoting clotting when delivered to the puncture site;

delivery structure having a distal end portion and being constructed and arranged to be mounted for longitudinal movement relative to said guide wire towards and away from the puncture site, said delivery structure having a fluid passageway open to said distal end portion thereof and communicated to said supply of fluid thrombogenic material;

a tubular puncture site engaging member having a distal end portion, said puncture site engaging member being mounted exteriorly of said delivery structure for longitudinal movement relative to said guide wire towards and away from the puncture site;

said locating device and said puncture site engaging member being constructed and arranged to be positioned with respect to one another such that said puncture site engaging member and said locating device can be moved together longitudinally towards the puncture site along the guide wire, said locating device being constructed and arranged to transmit a signal to the user indicating that the distal end portion of said puncture site engaging member is engaged with the tissue portion of the puncture site in surrounding relation with respect to the puncture;

said delivery structure being constructed and arranged such that the distal end portion of said delivery structure can be positioned adjacent the puncture site and the fluid thrombogenic material can be delivered from said supply to the puncture site through the fluid passageway of said delivery structure when the distal end portion of said puncture site engaging member is engaged with aforesaid tissue portion in surrounding relation with respect to the puncture;

said puncture site engaging member being constructed and arranged such that the distal end portion thereof will surround the fluid thrombogenic material being delivered to the puncture site so as to prevent the material from flowing away from the puncture site when the distal end portion of said puncture site engaging member is engaged with the tissue portion in surrounding relation with respect to the puncture, thereby allowing the material to promote clotting and seal the puncture.

2. A device according to claim 1, further comprising an expandable balloon member mounted to the exterior of said puncture site engaging member, said balloon member being constructed and arranged such that, when the distal end portion of said puncture site engaging member is engaged with the tissue portion in surrounding relation with respect to the puncture, fluid can be communicated to said balloon so as to expand said balloon member and cause said balloon member to press outwardly against the subcutaneous tissue to force the distal end portion of said puncture site engaging member against the tissue portion.

3. A device according to claim 1, wherein said locating device is a thin hollow tube constructed and arranged to be slidably mounted on said guide wire, said tube having a distal end portion with an opening and being constructed and arranged such that, when the distal end portion of said tube is positioned interiorly of the puncture site, fluid located interiorly of the puncture site will be allowed to flow into said opening and proximally through said tube, said thin hollow tube being constructed and arranged such that the distal end portion thereof will be positioned interiorly of said puncture site when said distal end portion of said puncture site engaging member is engaged with the tissue portion in surrounding relation with respect to the puncture such that the signal transmitted to the user by the locating device is the presence of fluid flowing proximally within said thin hollow tube.

4. A device according to claim 1, wherein the supply of fluid thrombogenic material comprises a supply of a first fluid solution and a supply of a second fluid solution and wherein said fluid passageway of said delivery structure includes a first fluid passageway communicated to the supply of said first fluid solution and open to the distal end portion of said delivery structure, and a second fluid passageway communicated to the supply of said second fluid solution and open to the distal end portion of said delivery structure;

said first and second fluid solutions being capable of promoting clotting when delivered to and mixed together at the puncture site.

5. A device according to claim 4, wherein said first fluid solution and said second fluid solution form a fibrin glue when mixed together.

6. A device according to claim 4, wherein said delivery structure comprises a tubular body member and first and second hollow tubes disposed inside said body member and communicated to said supply of the first fluid solution and said supply of the second fluid solution, respectively, said first and second fluid passageways being defined within said first and second hollow tubes, respectively.

7. A device according to claim 4, wherein said delivery structure comprises a syringe having first and second chambers with respective first and second exit ports, said first and second exit ports being communicated with first and second fluid passageways of said delivery structure, respectively, the supply of said first fluid solution being contained in said first chamber and the supply of said second fluid solution being contained in said second chambers, said syringe being constructed and arranged to expel said first and second solutions from the respective first and second chambers outwardly through said first and second exit ports and respectively into the first and second passageways of said delivery structure as a result of manual operation of said syringe.

8. A device according to claim 7, wherein said syringe comprises a single plunger constructed and arranged such that manually operating said single plunger will simultaneously expel said first and second fluid solutions from their respective first and second chambers.

9. A device according to claim 1, further comprising an outer sheath member slidably mounted on the exterior of said puncture site engaging member, said distal end portion of said puncture site engaging member being constructed and arranged to expand from a normal, unexpanded configuration to an expanded generally cone-shaped structure when unrestrained in a generally radial direction of said puncture site engaging member, said outer sheath member being constructed and arranged such that a distal end portion thereof can be slidably positioned over the distal end portion of said puncture site engaging member so as to prevent said puncture site engaging member distal end portion from expanding from the normal, unexpanded configuration thereof, said outer sheath member being constructed and arranged such that, after the locating device has transmitted the signal indicating that the distal end portion of said puncture site engaging member is engaged with the tissue portion in surrounding relation with respect to the puncture, the user can then move said outer sheath member longitudinally away from the puncture site so as to allow said distal end portion of said puncture site engaging member to expand from the normal, unexpanded configuration to the expanded generally cone-shaped structure.

10. A device according to claim 1, wherein the distal end portion of said puncture site engaging member comprises a flexible material and is constructed and arranged to expand from a normal, unexpanded configuration to an expanded cone-shaped configuration as the fluid thrombogenic material is being delivered to the puncture site as a result of the material occupying the space defined within the distal end portion of said puncture site engaging member.

11. A device according to claim 1, wherein said locating device comprises a tubular member having a distal end portion with a distal port and a proximal port spaced apart generally longitudinally and open to the exterior thereof, and first and second hollow tubes connected to said distal port and said proximal port, respectively;

said distal port and said first hollow tube being constructed and arranged such that, when the distal port is positioned interiorly of the puncture site, fluid located interiorly of the puncture site will be allowed to flow into said distal port and proximally through said first hollow tube;

said proximal port and said second hollow tube being constructed and arranged such that, when the proximal port is positioned interiorly of the puncture site, the fluid located interiorly of the puncture site will be allowed to flow into said proximal port and proximally through said second hollow tube;

said tubular member being positioned with respect to said puncture site engaging member such that only the distal port of the distal and proximal ports will be positioned interiorly of said puncture site when said distal end portion of said puncture site engaging member is engaged with the tissue portion in surrounding relation with respect to the puncture such that the signal transmitted to the user by the locating device indicating that the distal end portion of said puncture site engaging member is engaged with the tissue portion in surrounding relation with respect to the puncture is the presence of fluid flowing proximally within said first hollow tube and the absence of fluid flowing proximally within said second hollow tube.

12. A device according to claim 11, wherein said tubular member is an obturator constructed and arranged to substantially occlude the puncture when the distal end portion of said puncture site engaging member is engaged with the tissue portion in surrounding relation with respect to the puncture so as to substantially prevent fluid from flowing through the puncture.

13. A device according to claim 11, wherein said delivery structure comprises a tubular body member and wherein said tubular member of said locating device is slidably mounted within said body member, said tubular body member having a distal end portion comprising resiliently deformable material and defining an aperture therethrough, said distal end portion of said tubular body member being constructed and arranged such that said tubular member of said locating device can be moved distally with respect to said guide wire to an extended position wherein the resiliently deformable material of the distal end portion of said tubular body member is deformed outwardly with the tubular member extending distally through said aperture, said tubular body member being constructed and arranged such that said tubular member can be moved proximally with respect to said guide wire to a retracted position wherein the resiliently deformable material of the distal end portion of said tubular body member resiliently moves inwardly to close said aperture;

said tubular body member being constructed and arranged such that, when said tubular member is in said retracted position thereof, said tubular body member can be moved distally with respect to said guide wire so that the distal end portion thereof is engaged with and compresses the fluid thrombogenic material delivered to the puncture site.

14. A device according to claim 1, further comprising an obturator constructed and arranged to substantially occlude the puncture when the distal end portion of said puncture site engaging member is engaged with the tissue portion in surrounding relation with respect to the puncture so as to substantially prevent fluid from flowing through the puncture.

15. A device according to claim 1, wherein said delivery structure comprises a tubular body member and a hollow tube disposed inside said body member and communicated to said supply of fluid thrombogenic material, said fluid passageway of said delivery structure being defined within said hollow tube.

16. A device according to claim 1, wherein said locating device and said puncture site engaging member are constructed and arranged such that, after the distal end portion of said puncture site engaging member has been engaged with the tissue portion in surrounding relation with respect to the puncture, said locating member can be moved longitudinally along said guide wire away from the puncture site.

17. A device for percutaneously sealing an internal puncture site, the puncture being formed in a portion of a blood vessel wall and being accessible through a perforation formed through the skin and subcutaneous tissue of a living being with an elongated guide wire being inserted through the perforation, the puncture, and into the vessel, said device comprising:

a locating device constructed and arranged to be mounted for longitudinal movement relative to said guide wire towards and away from the puncture site;

a supply of fluid thrombogenic material which will be capable of promoting clotting when delivered to the puncture site;

delivery structure having a distal end portion and being constructed and arranged to be mounted for longitudinal movement relative to said guide wire towards and away from the puncture site, said delivery structure having a fluid passageway open to said distal end portion thereof and communicated to said supply of fluid thrombogenic material;

a tubular puncture site engaging member having a distal end portion, said puncture site engaging member being mounted exteriorly of said delivery structure for longitudinal movement relative to said guide wire towards and away from the puncture site;

said locating device and said puncture site engaging member being constructed and arranged to be positioned with respect to one another such that said puncture site engaging member and said locating device can be moved together longitudinally along the guide wire towards the puncture site, said locating device being constructed and arranged to transmit a signal to the user indicating that the distal end portion of said puncture site engaging member is engaged with the vessel wall portion in surrounding relation with respect to the puncture;

said delivery structure being constructed and arranged such that the distal end portion of said delivery structure can be positioned adjacent the puncture site and the fluid thrombogenic material can be delivered from said supply to the puncture site through the fluid passageway of said delivery structure when the distal end portion of said puncture site engaging member is engaged with the vessel wall portion in surrounding relation with respect to the puncture;

said puncture site engaging member being constructed and arranged such that the distal end portion thereof will surround the fluid thrombogenic material being delivered to the puncture site so as to prevent the material from flowing away from the puncture site when the distal end portion of said puncture site engaging member is engaged with the vessel wall portion in surrounding relation with respect to the puncture, thereby allowing the material to promote clotting and seal the puncture.

18. A device according to claim 17, further comprising an expandable balloon member mounted to the exterior of said puncture site engaging member, said balloon member being constructed and arranged such that, when the distal end portion of said puncture site engaging member is engaged with the vessel wall portion in surrounding relation with respect to the puncture, fluid can be communicated to said balloon so as to expand said balloon member and cause said balloon member to press outwardly against the subcutaneous tissue to force the distal end portion of said puncture site engaging member against the vessel wall portion.

19. A device according to claim 17, wherein said locating device is a thin hollow tube constructed and arranged to be slidably mounted on said guide wire, said tube having a distal end portion with an opening and being constructed and arranged such that, when the distal end portion of said tube is positioned inside the blood vessel, blood flowing through the vessel will be allowed to flow into said opening and proximally through said tube, said thin hollow tube being constructed and arranged such that the distal end portion thereof will be positioned inside the blood vessel when said distal end portion of said puncture site engaging member is engaged with the vessel portion in surrounding relation with respect to the puncture such that the signal transmitted to the user by the locating device is the presence of blood flowing proximally within said thin hollow tube.

20. A device according to claim 17, wherein the supply of fluid thrombogenic material comprises a supply of a first fluid solution and a supply of a second fluid solution and wherein said fluid passageway of said delivery structure includes a first fluid passageway communicated to the supply of said first fluid solution and open to the distal end portion of said delivery structure and a second fluid passageway communicated to the supply of said second fluid solution and open to the distal end portion of said delivery structure;

said first and second fluid solutions being capable of promoting clotting when delivered to and mixed together at the puncture site.

21. A device according to claim 20, wherein said first fluid solution and said second fluid solution form a fibrin glue when mixed together.

22. A device according to claim 20, wherein said delivery structure comprises a syringe having first and second chambers with respective first and second exit ports, each of said first and second exit ports being communicated with the first and second fluid passageways of said delivery structure, respectively the supply of said first fluid solution being contained in said first chamber and the supply of said second fluid solution being contained in said second chamber, said syringe being constructed and arranged to expel said first and second solutions from the respective first and second chambers outwardly through said exit ports and respectively into the first and second passageways of said delivery structure as a result of manual operation of said syringe.

23. A device according to claim 22, wherein said syringe comprises a single plunger constructed and arranged such that manually operating said single plunger will simultaneously expel said first and second fluid solutions from their respective first and second chambers.

24. A device according to claim 20, wherein said delivery structure comprises a tubular body member and first and second hollow tubes disposed inside said body member and communicated to said supply of the first fluid solution and said supply of the second fluid solution, respectively, said first and second fluid passageways being defined within said first and second hollow tubes, respectively.

25. A device according to claim 17, further comprising an outer sheath member slidably mounted on the exterior of said puncture site engaging member, said distal end portion of said puncture site engaging member being constructed and arranged to expand from a normal unexpanded configuration to an expanded generally cone-shaped structure when unrestrained in a generally radial direction of said puncture site engaging member, said outer sheath member being constructed and arranged such that a distal end portion thereof can be slidably positioned over the distal end portion of said puncture site engaging member so as to prevent said puncture site engaging member distal end portion from expanding from the normal, unexpanded configuration thereof, said outer sheath member being constructed and arranged such that, after the locating device has transmitted the signal indicating that the distal end portion of said puncture site engaging member is engaged with the surrounding vessel wall portion, the user can then move said outer sheath member longitudinally away from the puncture site so as to allow said distal end portion of said puncture site engaging member to expand from the normal unexpanded configuration to the expanded generally cone-shaped structure.

26. A device according to claim 17, wherein the distal end portion of said puncture site engaging member comprises a flexible material and is constructed and arranged to expand from a normal unexpanded configuration to an expanded cone-shaped configuration as the fluid thrombogenic material is being delivered to the puncture site as a result of the material occupying the space defined within the distal end portion of said puncture site engaging member.

27. A device according to claim 17, wherein said locating device comprises a tubular member having distal end portion with a distal port and a proximal port spaced apart generally longitudinally and open to the exterior thereof, and first and second hollow tubes connected to said distal port and said proximal port, respectively;

said distal port and said first hollow tube being constructed and arranged such that, when the distal port is positioned inside the blood vessel, fluid flowing through the blood vessel will be allowed to flow into said distal port and proximally through said first hollow tube;

said proximal port and said second hollow tube being constructed and arranged such that, when the proximal port is positioned inside the blood vessel, fluid flowing through the blood vessel will be allowed to flow into said proximal port and proximally through said second hollow tube;

said tubular member being positioned with respect to said puncture site engaging member such that only the distal port of the distal and proximal ports will be positioned inside the blood vessel when said distal end portion of said puncture site engaging member is engaged with the surrounding vessel portion such that the signal transmitted to the user by the locating device indicating that the distal end portion of said puncture site engaging member is engaged with the vessel wall portion in surrounding relation with respect to the puncture is the presence of blood flowing proximally within said first hollow tube and the absence of blood flowing proximally within said second hollow tube.

28. A device according to claim 27, wherein said tubular member is an obturator constructed and arranged to substantially occlude the puncture when the distal end portion of said puncture site engaging member is engaged with the vessel wall portion in surrounding relation with respect to the puncture so as to substantially prevent blood from flowing out of the blood vessel through the puncture.

29. A device according to claim 27, wherein said delivery structure comprises a tubular body member and wherein said tubular member of said locating device is slidably mounted within said body member, said tubular body member having a distal end portion comprising resiliently deformable material and defining an aperture therethrough, said distal end portion of said tubular body member being constructed and arranged such that said tubular member of said locating device can be moved distally with respect to said guide wire to an extended position wherein the resiliently deformable material of the distal end portion of said tubular body member is deformed outwardly with the tubular member extending distally through said aperture, said tubular body member being constructed and arranged such that said tubular member can be moved proximally with respect to said guide wire to a retracted position wherein the resiliently deformable material of the distal end portion of said tubular body member resiliently moves inwardly to close said aperture;

said tubular body member being constructed and arranged such that, when said tubular member is in said retracted position thereof, said tubular body member can be moved distally with respect to said guide wire so that the distal end portion thereof is engaged with and compresses the fluid thrombogenic material delivered to the puncture site.

30. A device according to claim 17, further comprising an obturator constructed and arranged to substantially occlude the puncture when the distal end portion of said puncture site engaging member is engaged with the vessel wall portion in surrounding relation with respect to the puncture so as to substantially prevent blood from flowing out of the blood vessel through the puncture.

31. A device according to claim 17, wherein said delivery structure comprises a tubular body member and a hollow tube disposed inside said body member and communicated to said supply of fluid thrombogenic material, said fluid passageway of said delivery structure being defined within said hollow tube.

32. A device according to claim 17, wherein said locating device and said puncture site engaging member are constructed and arranged such that, after the distal end portion of said puncture site engaging member has been engaged with the vessel wall portion in surrounding relation with respect to the puncture, said locating member can be moved longitudinally along said guide wire away from the puncture site.

33. A method for percutaneously sealing of an internal puncture site comprising a tissue portion having a puncture formed therethrough, the puncture site being accessible through a perforation formed through the skin and subcutaneous tissue of a living being with an elongated guide wire being inserted through the perforation and into the puncture, said method comprising:

providing a locating device;

providing a supply of fluid thrombogenic material which will be capable of promoting clotting when delivered to the puncture site;

providing delivery structure having a distal end portion, said delivery structure having a fluid passageway open to said distal end portion thereof and communicated to said supply of fluid thrombogenic material;

providing a puncture site engaging member having a distal end portion, said puncture site engaging member being mounted exteriorly of said delivery structure a nd being positioned with respect to said locating device such that said puncture site engaging member and said locating device can be moved longitudinally together along the guide wire toward the puncture site;

moving said puncture site engaging member an d said locating device longitudinally along said guide wire towards the puncture site until said locating device transmits a signal to the user indicating that the distal end portion of said puncture site engaging member is engaged with a tissue portion of the puncture site in surrounding relation with respect to th e puncture;

after said locating device has signaled the user that the distal end portion of said puncture site engaging member is engaged with the tissue portion in surrounding relation with respect to the puncture, delivering the fluid thrombogenic material from said supply to the puncture site through said fluid passageway; and maintaining the distal end portion of said puncture site engaging member in engagement with the tissue portion as the fluid thrombogenic material is being delivered such that the distal end portion of said puncture site engaging member surrounds the fluid thrombogenic material being delivered to the puncture site so as to prevent the material from flowing away from the puncture site, thereby allowing the material to promote clotting and seal the puncture.

34. A method according to claim 33, wherein said puncture site engaging member has an expandable balloon member mounted to the exterior thereof and further comprising:

after said locating device has transmitted the signal indicating that the distal end portion of said puncture site engaging member is engaged with the tissue portion in surrounding relation with respect to the puncture, communicating fluid to said balloon member so as to expand said balloon member and cause said balloon member to press outwardly against the subcutaneous tissue to force the distal end portion of said puncture site engaging member against the tissue portion.

35. A method according to claim 33, wherein said locating device is a thin hollow tube constructed and arranged to be slidably mounted on said guide wire, said tube having a distal end portion with an opening, and wherein moving said puncture site engaging member and said locating device together until said locating device transmits said signal comprises:

moving said thin hollow tube and said locating device longitudinally along said guide wire towards the puncture site until the distal end portion of said tube is positioned interiorly of said puncture site such that fluid located interiorly of the puncture site will be allowed to flow proximally within said thin hollow tube, the signal transmitted to the user by the locating device being the presence of the fluid flowing proximally within said thin hollow tube.

36. A method according to claim 33, wherein the supply of fluid thrombogenic material comprises a supply of a first fluid solution and a supply of a second fluid solution and wherein said fluid passageway of said delivery structure includes a first fluid passageway communicated to the supply of said first fluid solution and open to the distal end portion of said delivery structure and a second fluid passageway communicated to the supply of said second fluid solution and open to the distal end portion of said delivery structure, said first and second fluid solutions being capable of promoting clotting when delivered to and mixed together at the puncture site;

wherein delivering the fluid thrombogenic material from said supply to the puncture site through said fluid passageway comprises delivering said first fluid solution and said second fluid solution to the puncture site through said first and second fluid passageways, respectively, such that the first and second fluid solutions mix at the puncture site to promote clotting and seal the puncture.

37. A method according to claim 36, wherein said first fluid solution and said second fluid solution form a fibrin glue when mixed together.

38. A method according to claim 36, wherein said delivery structure comprises a syringe having first and second chambers with respective first and second exit ports, said first and second exit ports being respectively communicated with the first and second fluid passageways of said delivery structure, the supply of said first fluid solution being contained in said first chamber and the supply of said second fluid solution being contained in said second chamber, wherein delivering said fluid thrombogenic material comprises manually operating said syringe so as to expel said first and second solutions from the respective first and second chambers outwardly through said respective first and second exit ports and into the respective first and second passageways of said delivery structure.

39. A method according to claim 38, wherein said syringe comprises a single plunger constructed and arranged such that manually operating said single plunger will simultaneously expel said first and second fluid solutions from their respective chambers.

40. A method according to claim 36, wherein said delivery structure comprises a tubular body member, and first and second hollow tubes disposed inside said body member and communicated to said supply of the first fluid solution and said supply of the second fluid solution, respectively, said first and second fluid passageways being defined within said first and second hollow tubes, respectively.

41. A method according to claim 33, wherein said distal end portion of said puncture site engaging member is constructed and arranged to expand from a normal unexpanded configuration to an expanded generally cone-shaped structure when unrestrained in a generally radial direction of said puncture site engaging member, said method further comprising:

providing an outer sheath member slidably mounted on the exterior of said puncture site engaging member, said outer sheath member being positioned over the distal end portion of said puncture site engaging member so as to prevent said puncture site engaging member distal end portion from expanding from the normal unexpanded configuration thereof; and after the locating device has transmitted the signal indicating that the distal end portion of said puncture site engaging member is engaged with the tissue portion in surrounding relation with respect to the puncture, moving said outer sheath member longitudinally away from the puncture site so as to allow said distal end portion of said puncture site engaging member to expand from the normal unexpanded configuration to the expanded generally cone-shaped structure.

42. A method according to claim 41, further comprising:

providing an obturator;

positioning said obturator within the puncture such that said obturator substantially occludes the puncture so as to substantially prevent fluid from flowing through the puncture when the distal end portion of said puncture site engaging member is engaged with the tissue portion in surrounding relation with respect to the puncture.

43. A method according to claim 33, wherein the distal end portion of said puncture site engaging member comprises a flexible material and is constructed and arranged to expand from a normal unexpanded configuration to an expanded cone-shaped configuration as the fluid thrombogenic material is being delivered to the puncture site as a result of the material occupying the space defined within the distal end portion of said puncture site engaging member.

44. A method according to claim 33, wherein said locating device comprises a tubular member having a distal end portion with a distal port and a proximal port spaced apart generally longitudinally and open to the exterior thereof, and first and second hollow tubes connected to said distal port and said proximal port, respectively, said distal port and said first hollow tube being constructed and arranged such that, when the distal port is positioned interiorly of the puncture site, fluid located interiorly of the puncture site will be allowed to flow into said distal port and proximally through said first hollow tube, said proximal port and said second hollow tube being constructed and arranged such that, when the proximal port is positioned interiorly of the puncture site, fluid located interiorly of the puncture site will be allowed to flow into said proximal port and proximally through said second hollow tube, wherein moving said puncture site engaging member and said locating device together until said locating device transmits said signal comprises:

moving said tubular member and said puncture site engaging member longitudinally along said guide wire towards the puncture site until only the distal port of said distal and proximal ports is positioned interiorly of said puncture site such that fluid flowing interiorly of the puncture site flows proximally within said first hollow tube, the signal transmitted to the user by the locating device being the simultaneous presence of the fluid flowing proximally within said first hollow tube and absence of fluid flowing within said second hollow tube.

45. A method according to claim 44, wherein said tubular member is an obturator and wherein moving said puncture site engaging member and said locating device together until said locating device transmits said signal comprises:

positioning said obturator within said puncture such that said obturator occludes the puncture so as to substantially prevent fluid from flowing through the puncture.

46. A method according to claim 45, wherein said delivery structure comprises a tubular body member, and a hollow tube disposed inside said body member and communicated to said supply of fluid thrombogenic material, said fluid passageway of said delivery structure being defined within said hollow tube.

47. A method according to claim 44, wherein said delivery structure comprises a tubular body member and wherein said tubular member of said locating device is slidably mounted within said body member, said tubular body member having a distal end portion comprising resiliently deformable material and defining an aperture therethrough, said distal end portion of said tubular body member being constructed and arranged such that said tubular member can be moved distally with respect to said guide wire to an extended position wherein the resiliently deformable material of the distal end portion of said tubular body member is deformed outwardly with the tubular member extending distally of said aperture, said tubular body member being constructed and arranged such that said tubular member can be moved proximally with respect to said guide wire to a retracted position wherein the resiliently deformable material of the distal end portion of said tubular body member resiliently moves inwardly to close said aperture;

said tubular body member being constructed and arranged such that, when said tubular member is in said retracted position thereof, said tubular body member can be moved distally with respect to said guide wire so that the distal end portion thereof is engaged with and compresses the fluid thrombogenic material delivered to the puncture site.

48. A method according to claim 33, wherein said locating device and said puncture site engaging member are releaseably fixedly positioned with respect to one another and wherein said method further comprises:

after the locating device has transmitted the signal that the distal end portion of said puncture site engaging member has been engaged with the tissue portion in surrounding relation with respect to the puncture, moving said locating member longitudinally along said guide wire away from the puncture site.

49. A method for percutaneously sealing of an internal puncture site, the internal puncture site being formed in the wall of a blood vessel and being accessible through a perforation formed through the skin and subcutaneous tissue of a living being with an elongated guide wire being inserted through the perforation, the puncture, and into the vessel, said method comprising:

providing a locating device;

providing a supply of fluid thrombogenic material which will be capable of promoting clotting when delivered to the puncture site;

providing delivery structure having a distal end portion, said delivery structure having a fluid passageway open to said distal end portion thereof and communicated to said supply of fluid thrombogenic material;

providing a puncture site engaging member having a distal end portion, said puncture site engaging member being mounted exteriorly of said delivery structure and being positioned with respect to said locating device such that said puncture site engaging member and said locating device can be moved longitudinally together along the guide wire toward the puncture site;

moving said puncture site engaging member and said locating device longitudinally along said guide wire towards the puncture site until said locating device transmits a signal to the user indicating that the distal end portion of said puncture site engaging member is engaged with a vessel wall portion in surrounding relation with respect to the puncture;

after said locating device has transmitted the signal indicating that the distal end portion of said puncture site engaging member is engaged with the vessel wall portion in surrounding relation with respect to the puncture, delivering the fluid thrombogenic material from said supply to the puncture site through said fluid passageway;

maintaining the distal end portion of said puncture site engaging member in engagement with the vessel wall portion as the fluid thrombogenic material is being delivered such that the distal end portion of said puncture site engaging member surrounds the fluid thrombogenic material being delivered to the puncture site so as to prevent the material from flowing away from the puncture site, thereby allowing the material to promote clotting and seal the puncture.

50. A method according to claim 49, wherein said puncture site engaging member has an expandable balloon member mounted to the exterior thereof and further comprising:

after said locating device has transmitted the signal indicating that the distal end portion of said puncture site engaging member is engaged with the vessel wall portion in surrounding relation with respect to the puncture, communicating fluid to said balloon member so as to expand said balloon member and cause said balloon member to press outwardly against the subcutaneous tissue to force the distal end portion of said puncture site engaging member against the vessel wall portion.

51. A method according to claim 49, wherein said locating device is a thin hollow tube constructed and arranged to be slidably mounted on said guide wire, said tube having a distal end portion with an opening, and wherein moving said puncture site engaging member and said locating device together until said locating device transmits said signal comprises:

moving said thin hollow tube and said locating device longitudinally along said guide wire towards the puncture site until the distal end portion of said tube is positioned inside the blood vessel such that fluid flowing through the blood vessel will be allowed to flow proximally within said thin hollow tube, the signal transmitted to the user by the locating device being the presence of the blood flowing proximally within said thin hollow tube.

52. A method according to claim 49, wherein the supply of fluid thrombogenic material comprises a supply of a first fluid solution and a supply of a second fluid solution and wherein said fluid passageway of said delivery structure includes a first fluid passageway communicated to the supply of said first fluid solution and open to the distal end portion of said delivery structure and a second fluid passageway communicated to the supply of said second fluid solution and open to the distal end portion of said delivery structure, said first and second fluid solutions being capable of promoting clotting when delivered to and mixed together at the puncture site;

wherein delivering the fluid thrombogenic material from said supply to the puncture site through said fluid passageway comprises delivering said first fluid solution and said second fluid solution to the puncture site through said first and second fluid passageways, respectively, such that the first and second fluid solutions mix at the puncture site to promote clotting and seal the puncture.

53. A method according to claim 52, wherein said first fluid solution and said second fluid solution form a fibrin glue when mixed together.

54. A method according to claim 52, wherein said delivery structure comprises a syringe having first and second chambers with respective first and second exit ports, said first and second exit ports being respectively communicated with the first and second fluid passageways of said delivery structure, the supply of said first fluid solution being contained in said first chamber and the supply of said second fluid solution being contained in said second chamber, wherein delivering said fluid thrombogenic material comprises manually operating said syringe so as to expel said first and second solutions from the respective first and second chambers outwardly through said respective first and second exit ports and into the respective first and second passageways of said delivery structure.

55. A method according to claim 54, wherein said syringe comprises a single plunger constructed and arranged such that manually operating said single plunger will simultaneously expel said first and second fluid solutions from their respective first and second chambers.

56. A method according to claim 52, wherein said delivery structure comprises a tubular body member and first and second hollow tubes disposed inside said body member and communicated to said supply of the first fluid solution and said supply of the second fluid solution, respectively, said first and second fluid passageways being defined within said first and second hollow tubes, respectively.

57. A method according to claim 49, wherein said distal end portion of said puncture site engaging member is constructed and arranged to expand from a normal unexpanded configuration to an expanded generally cone-shaped structure when unrestrained in a generally radial direction of said puncture site engaging member, said method further comprising:

providing an outer sheath member slidably mounted on the exterior of said puncture site engaging member, said outer sheath member being positioned over the distal end portion of said puncture site engaging member so as to prevent said puncture site engaging member distal end portion from expanding from the normal unexpanded configuration thereof; and after the locating device has transmitted the signal indicating that the distal end portion of said puncture site engaging member is engaged with the vessel wall portion, moving said outer sheath member longitudinally away from the puncture site so as to allow said distal end portion of said puncture site engaging member to expand from the normal unexpanded configuration to the expanded generally cone-shaped structure.

58. A method according to claim 49, wherein the distal end portion of said puncture site engaging member comprises a flexible material and is constructed and arranged to expand from a normal unexpanded configuration to an expanded cone-shaped configuration as the fluid thrombogenic material is being delivered to the puncture site as a result of the material occupying the space defined within the distal end portion of said puncture site engaging member.

59. A method according to claim 49, wherein said locating device comprises a tubular member having a distal end portion with a distal port and a proximal port spaced apart generally longitudinally and open to the exterior thereof, and first and second hollow tubes connected to said distal port and said proximal port, respectively, said distal port and said first hollow tube being constructed and arranged such that, when the distal port is positioned inside the blood vessel, blood flowing through the blood vessel will be allowed to flow into said distal port and proximally through said first hollow tube, said proximal port and said second hollow tube being constructed and arranged such that, when the proximal port is positioned inside the blood vessel, blood flowing through the blood vessel will be allowed to flow into said proximal port and proximally through said second hollow tube, wherein moving said puncture site engaging member and said locating device together until said locating device transmits said signal comprises:

moving said tubular member and said puncture site engaging member longitudinally along said guide wire towards the puncture site until only the distal port of said distal and proximal ports is positioned inside said blood vessel such that blood flowing through the blood vessel will be allowed to flow proximally within said first hollow tube, the signal transmitted to the user by the locating device being the presence of the blood flowing proximally within said first hollow tube and the absence of blood flowing within said second hollow tube.

60. A method according to claim 59, wherein said tubular member is an obturator and wherein moving said puncture site engaging member and said locating device together until said locating device transmits said signal comprises:

positioning said obturator within said puncture such that said obturator occludes the puncture so as to substantially prevent blood from flowing out of the blood vessel through the puncture.

61. A method according to claim 49, further comprising:
providing an obturator;
positioning said obturator within the puncture such that said obturator substantially occludes the puncture so as to substantially prevent blood from flowing out of the blood vessel through the puncture when the distal end portion of said puncture site engaging member is engaged with the vessel wall portion in surrounding relation with respect to the puncture.

62. A method according to claim 59, wherein said delivery structure comprises a tubular body member and wherein said tubular member of said locating device is slidably mounted within said body member, said tubular body member having a distal end portion comprising resiliently deformable material and defining an aperture therethrough, said distal end portion of said tubular body member being constructed and arranged such that said tubular member can be moved distally with respect to said guide wire to an extended position wherein the resiliently deformable material of the distal end portion of said tubular body member is deformed outwardly with the tubular member extending distally of said aperture, said tubular body member being constructed and arranged such that said tubular member can be moved proximally with respect to said guide wire to a retracted position wherein the resiliently deformable material of the distal end portion of said tubular body member resiliently moves inwardly to close said aperture;

said tubular body member being constructed and arranged such that, when said tubular member is in said retracted position thereof, said tubular body member can be moved distally with respect to said guide wire so that the distal end portion thereof is engaged with and compresses the fluid thrombogenic material delivered to the puncture site.

63. A method according to claim 60, wherein said delivery structure comprises a tubular body member and a hollow tube disposed inside said body member and communicated to said supply of fluid thrombogenic material, said fluid passageway of said delivery structure being defined within said hollow tube.

64. A method according to claim 49, wherein said locating device and said puncture site engaging member are releaseably fixedly positioned with respect to one another and wherein said method further comprises:

after the locating device has transmitted the signal that the distal end portion of said puncture site engaging member has been engaged with the vessel wall portion in surrounding relation with respect to the puncture, moving said locating member longitudinally along said guide wire away from the puncture site.

65. A sealing device for percutaneously sealing of an internal puncture site comprising a tissue portion having a puncture formed therethrough, the puncture site being accessible through a perforation formed through the skin and subcutaneous tissue of a living being with an elongated guide wire being inserted though the perforation and into the puncture, said device comprising:

closure structure constructed and arranged to seal the puncture in response to manual operation when said sealing device is in a proper operating position with respect to the puncture site; and a locating device having a distal end portion with a distal port and a proximal port spaced apart generally longitudinally and open to the exterior of said distal end portion thereof, said locating device being constructed and arranged to be mounted for longitudinal movement relative to the guide wire towards and away from the puncture site and defining first and second fluid passageways connected to said locating distal port and said proximal port, respectively;

said distal port and said first fluid passageway being constructed and arranged such that, when the distal port is positioned interiorly of the puncture site, fluid located interiorly of the puncture site will be allowed to flow into said distal port and proximally through said first fluid passageway;

said proximal port and said second fluid passageway being constructed and arranged such that, when the proximal port is positioned interiorly of the puncture site, the fluid located interiorly of the puncture site will be allowed flow into said proximal port and proximally through said second fluid passageway;

said locating device being constructed and arranged to be moved longitudinally along the guide wire towards the puncture site, said locating device being constructed and arranged such that only the distal port of the distal and proximal ports will be positioned interiorly of the puncture site when said sealing device has reached the proper operating position thereof with respect to the puncture site so that the presence of fluid flowing proximally within said first fluid passageway and the absence of fluid flowing proximally within said second fluid passageway will indicate that the sealing device is in the proper operating position with respect to the puncture site.

66. A sealing device according to claim 65, wherein said locating device and said closure structure are constructed and arranged to be positioned with respect to one another such that said locating device and said closure structure can be moved together longitudinally along the guide wire towards the puncture site until said locating device indicates that said sealing device is in the proper operating position thereof.

67. A device according to claim 66, wherein said locating device comprises a tubular member having distal end portion, said proximal and distal ports being located on the distal end portion of said tubular member.

68. A device according to claim 67, wherein said locating device comprises first and second hollow tubes connected to said distal and proximal ports, respectively, said first and second hollow tubes respectively defining said first and second fluid passageways therein.

69. A device according to claim 68, wherein the user can view said first and second hollow tubes to visually verify the presence or absence of fluid therein.

70. A device according to claim 66, wherein said closure structure comprises:

a supply of fluid thrombogenic material which will be capable of promoting clotting when delivered to the puncture site;

delivery structure having a distal end portion and being constructed and arranged to be mounted for longitudinal movement relative to said guide wire towards and away from the puncture site, said delivery structure having a fluid passageway open to said distal end portion thereof and communicated to said supply of fluid thrombogenic material;

a tubular puncture site engaging member having a distal end portion, said puncture site engaging member being mounted exteriorly of said delivery structure for longitudinal movement relative to said guide wire towards and away from the puncture site;

said locating device and said puncture site engaging member being constructed and arranged to be positioned with respect to one another such that said puncture site engaging member and said locating device can be moved together longitudinally along the guide wire towards the puncture site, said locating device being constructed and arranged such that only the distal port of the distal and proximal ports will be positioned interiorly of the puncture site when said puncture site engaging member is in the proper operating position with the distal end portion thereof being engaged with the tissue portion in surrounding relation with respect to the puncture so that the presence of fluid flowing proximally within said first fluid passageway and the absence of fluid flowing proximally within said second fluid passageway will indicate that the closure structure is in the proper operating position with respect to the puncture site;

said delivery structure being constructed and arranged such that the distal end portion of said delivery structure can be positioned adjacent the puncture site and the fluid thrombogenic material can be delivered from said supply to the puncture site through the fluid passageway of said delivery structure when the distal end portion of said puncture site engaging member is engaged with in surrounding relation with respect to the puncture site tissue portion;

said puncture site engaging member being constructed and arranged such that the distal end portion thereof will surround the fluid thrombogenic material being delivered to the puncture site so as to prevent the material from flowing away from the puncture site when the distal end portion of said puncture site engaging member is engaged with the tissue portion in surrounding relation with respect to the puncture, thereby allowing the material to promote clotting and seal the puncture.

71. A sealing device for percutaneously sealing of an internal puncture site, the puncture site being formed through the a portion of a blood vessel wall and being accessible through a perforation formed through the skin and subcutaneous tissue of a living being with an elongated guide wire being inserted through the perforation, the puncture, and into the vessel, said device comprising:

closure structure constructed and arranged to seal the puncture in response to manual operation when said sealing device is in a proper operating position with respect to the puncture site; and a locating device having a distal end portion with a distal port and a proximal port spaced apart generally longitudinally and open to the exterior of said distal end portion thereof, said locating device being constructed and arranged to be mounted for longitudinal movement relative to the guide wire towards and away from the puncture site and defining first and second fluid passageways connected to said distal port and said proximal port, respectively;

said distal port and said first fluid passageway being constructed and arranged such that, when the distal port is positioned inside the blood vessel, blood flowing through the blood vessel will be allowed to flow into said distal port and proximally through said first fluid passageway;

said proximal port and said second fluid passageway being constructed and arranged such that, when the proximal port is positioned inside the blood vessel, blood flowing through the puncture site will be allowed to flow into said proximal port and proximally through said second fluid passageway;

said locating device being constructed and arranged to be moved longitudinally along the guide wire towards the puncture site, said locating device being constructed and arranged such that only the distal port of the distal and proximal ports will be positioned inside the blood vessel when said sealing device has reached the proper operating position thereof with respect to the puncture site so that the presence of blood flowing proximally within said first fluid passageway and the absence of blood flowing proximally within said second fluid passageway will indicate that the sealing device is in the proper operating position with respect to the puncture site.

72. A sealing device according to claim 71, wherein said locating device and said closure structure are constructed and arranged to be positioned with respect to one another such that said locating device and said closure structure can be moved together longitudinally along the guide wire towards the puncture site until said locating device indicates that said sealing device is in the proper operating position thereof.

73. A device according to claim 72, wherein said locating device comprises a tubular member having distal end portion, said proximal and distal ports being located on the distal end portion of said tubular member.

74. A device according to claim 73, wherein said locating device comprises first and second hollow tubes connected to said distal and proximal ports, respectively, said first and second hollow tubes respectively defining said first and second fluid passageways therein.

75. A device according to claim 74, wherein the user can view said first and second hollow tubes to visually verify the presence or absence of blood therein.

76. A device according to claim 72, wherein said closure structure comprises:

- a supply of fluid thrombogenic material which will be capable of promoting clotting when delivered to the puncture site;
- delivery structure having a distal end portion and being constructed and arranged to be mounted for longitudinal movement relative to said guide wire towards and away from the puncture site, said delivery structure having a fluid passageway open to said distal end portion thereof and communicated to said supply of fluid thrombogenic material;
- a tubular puncture site engaging member having a distal end portion, said puncture site engaging member being mounted exteriorly of said delivery structure for longitudinal movement relative to said guide wire towards and away from the puncture site;
- said locating device and said puncture site engaging member being constructed and arranged to be positioned with respect to one another such that said puncture site engaging member and said locating device can be moved together longitudinally towards the puncture site, said locating device being constructed and arranged such that only the distal port of the distal and proximal ports will be positioned inside the blood vessel when said puncture site engaging member is in the proper operating position with the distal end portion thereof being engaged with the vessel wall portion in surrounding relation with respect to the puncture so that the presence of blood flowing proximally within said first fluid passageway and the absence of blood flowing proximally within said second fluid passageway will indicate that the closure structure is in the proper operating position with respect to the puncture site;
- said delivery structure being constructed and arranged such that the distal end portion of said delivery structure can be positioned adjacent the puncture site and the fluid thrombogenic material can be delivered from said supply to the puncture site through the fluid passageway of said delivery structure when the distal end portion of said puncture site engaging member is engaged with in surrounding relation with respect to the puncture vessel wall portion;
- said puncture site engaging member being constructed and arranged such that the distal end portion thereof will surround the fluid thrombogenic material being delivered to the puncture site so as to prevent the material from flowing away from the puncture site when the distal end portion of said puncture site engaging member is engaged with the vessel wall portion in surrounding relation with respect to the puncture, thereby allowing the material to promote clotting and seal the puncture.

* * * * *